(12) United States Patent
Hershkowitz et al.

(10) Patent No.: US 9,969,941 B2
(45) Date of Patent: May 15, 2018

(54) HYDROCARBON CONVERSION PROCESS

(71) Applicant: ExxonMobil Chemical Patents Inc., Baytown, TX (US)

(72) Inventors: Frank Hershkowitz, Basking Ridge, NJ (US); Paul F. Keusenkothen, Houston, TX (US); Jeffrey W. Frederick, Spring Mills, PA (US); Richard J. Basile, Rockaway, NJ (US); John W. Fulton, Annandale, VA (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 171 days.

(21) Appl. No.: 15/196,771

(22) Filed: Jun. 29, 2016

(65) Prior Publication Data
US 2016/0304790 A1   Oct. 20, 2016

Related U.S. Application Data

(62) Division of application No. 14/878,746, filed on Oct. 8, 2015, now Pat. No. 9,447,324, which is a division of application No. 13/588,821, filed on Aug. 17, 2012, now Pat. No. 9,187,382.

(60) Provisional application No. 61/538,476, filed on Sep. 23, 2011.

(30) Foreign Application Priority Data
Nov. 18, 2011   (EP) ................... 11189648

(51) Int. Cl.
*C07C 4/02* (2006.01)
*C07C 4/04* (2006.01)
*C10G 9/16* (2006.01)
*C10G 9/18* (2006.01)
*C07C 5/333* (2006.01)
*C07C 5/35* (2006.01)
*C10G 9/26* (2006.01)
*B01J 19/24* (2006.01)
*C07C 5/327* (2006.01)
*C10B 23/00* (2006.01)
*C10B 27/06* (2006.01)
(Continued)

(52) U.S. Cl.
CPC ............ *C10G 9/16* (2013.01); *B01J 19/2485* (2013.01); *C07C 5/327* (2013.01); *C07C 5/333* (2013.01); *C07C 5/35* (2013.01); *C10B 23/00* (2013.01); *C10B 27/06* (2013.01); *C10B 43/10* (2013.01); *C10B 47/02* (2013.01); *C10G 9/18* (2013.01); *C10G 9/26* (2013.01); *B01J 2219/00164* (2013.01); *B01J 2219/2411* (2013.01); *B01J 2219/2419* (2013.01); *B01J 2219/2434* (2013.01); *C10G 2400/20* (2013.01)

(58) Field of Classification Search
CPC ................... C07C 4/02; C07C 4/04
USPC ............. 585/648, 613, 634, 910, 922
See application file for complete search history.

(56) References Cited

U.S. PATENT DOCUMENTS 2,692,819 A   10/1954   Hasche et al.
2,845,335 A   7/1958    Hasche
3,024,094 A   3/1962    Coberly
(Continued)

FOREIGN PATENT DOCUMENTS

WO   2009/126357   10/2009

*Primary Examiner* — Thuan D Dang

(57) ABSTRACT

The invention relates to a process for converting hydrocarbons into unsaturated products such as acetylene and/or ethylene. The invention also relates to converting acetylene to olefins such as ethylene and/or propylene, to polymerizing the olefins, and to equipment useful for these processes.

7 Claims, 8 Drawing Sheets

(51) Int. Cl.
*C10B 47/02* (2006.01)
*C10B 43/10* (2006.01)

(56) References Cited

U.S. PATENT DOCUMENTS

| | | |
|---|---|---|
| 3,093,697 A | 6/1963 | Kasbohm et al. |
| 7,491,250 B2 | 2/2009 | Hershkowitz et al. |
| 7,815,873 B2 | 10/2010 | Sankaranarayanan et al. |
| 7,846,401 B2 | 12/2010 | Hershkowitz et al. |
| 7,943,808 B2 | 5/2011 | Hershkowitz et al. |
| 2011/0008226 A1 | 1/2011 | Hershkowitz et al. |
| 2011/0009681 A1 | 1/2011 | Hershkowitz et al. |

HYDROCARBON CONVERSION PROCESS

CROSS REFERENCE TO RELATED APPLICATIONS

This application is a divisional of and claims priority to U.S. application Ser. No. 13/588,821 filed Aug. 17, 2012 which granted as U.S. Pat. No. 9,187,382 on Nov. 17, 2015, and also claims priority to Provisional Application No. 61/538,476 (2011EM212) filed on Sep. 23, 2011, EP Application No. 11189648.6 filed on Nov. 18, 2011, and U.S. application Ser. No. 14/878,746 filed Oct. 8, 2015, the disclosures of which are incorporated herein by reference in their entireties.

FIELD

The invention relates to a process for converting hydrocarbons into unsaturated products such as acetylene and/or ethylene. The invention also relates to converting acetylene to olefins such as ethylene and/or propylene, to polymerizing the olefins, and to equipment useful for these processes.

BACKGROUND

U.S. Pat. No. 2,845,335 discloses a four-step process for converting a hydrocarbon stream to a mixture comprising unsaturated hydrocarbon. The reactor system comprises four similar regenerative reactors, with reactors one and two comprising a first parallel reactor pair which are separated from a second parallel reactor pair (reactors three and four) by at least one mixing region. The reactor system is preheated before the first step of the process.

In one embodiment, the reference discloses a first step involving flowing a hydrocarbon through the first reactor pair toward the second reactor pair, with a first portion of the hydrocarbon flowing through reactor one and a second portion flowing through reactor two. Pyrolysis products flow away from the mixing region, through the second reactor pair, a portion of the pyrolysis products being deposited as coke in reactors one-four. In a second step, fuel and air are conducted toward the mixing region, the fuel being conducted through reactor three and the air being conducted through reactor four. The fuel and air combust in the mixing region, with the combustion products flowing away from the mixing region through the first reactor pair (a portion of the combustion products flowing through each of reactors one and two), thereby (i) heating the reactor system for step 3 and (ii) oxidizing coke deposited in reactors one, two, and four. The third step is similar to the first step, with pyrolysis products flowing away from the mixing region, through the second reactor pair and again depositing coke in reactors one-four. In a fourth step, fuel and air are again conducted toward the mixing region, but now the fuel is conducted through reactor four and the air is conducted through reactor three (the reverse of step two). The fuel and air combust in the mixing region, with the combustion products flowing away from the mixing region through the first reactor pair, thereby (i) heating the reactor system for step one and (ii) oxidizing coke deposited in reactors one, two, and three.

It is desired to increase the efficiency of the process.

SUMMARY OF THE INVENTION

In an embodiment, the invention relates to a hydrocarbon conversion process, comprising:

(A) heating at least a portion of a reactor to a temperature ≥800° C., the reactor comprising first and second channels;

(B) providing a first mixture to the heated reactor, the first mixture comprising hydrocarbon, wherein at least a portion of the hydrocarbon includes alkane;

(C) exposing the first mixture to a temperature ≥800° C. in the heated reactor and abstracting sufficient heat from the reactor to convert at least a portion of the first mixture's alkane to combustible non-volatiles and unsaturated hydrocarbon;

(D) transferring at least a portion of the unsaturated hydrocarbon away from the reactor via the first and second channels, at least a portion of the combustible non-volatiles being deposited in the first and second channels during the transfer; and (E) repeating steps (A)-(D); wherein step (A) includes:

(i) a first time interval during which fuel and oxidant exothermically react in the reactor, the fuel being provided via the first channel and the oxidant being provided via the second channel, in order to
  (a) replace at least a portion of the heat abstracted during step (C) and
  (b) combust at least a portion of the combustible non-volatiles in the second channel; and (ii) a second time interval during which additional oxidant is provided to the reactor via the first channel in order to combust at least a portion of the combustible non-volatiles in the first channel.

In another embodiment, the invention relates to a regenerative, reverse-flow pyrolysis reactor comprising, (a) first and second reactors, each comprising a unitary reactor bed;
(b) a mixing region located between the first and second reactors;
(c) first and second channels located within the first reactor, the first and second channels being thermally-connected, substantially independent flow-paths;
(d) a third channel located within the second reactor; and
(e) first valve means for directing to the mixing region
  (i) a first reactant via the first channel during a first time interval,
  (ii) a second reactant via a second channel during the first time interval, and
  (iii) a first portion of the second reactant via the first channel and a second portion of the second reactant via the second channel during a second time interval.

In yet another embodiment, the invention relates to a process for removing combustible non-volatiles from a reactor system, comprising:

(A) depositing combustible non-volatiles during a first conversion step, the combustible non-volatiles being deposited in first and second conduits of a first reactor, the first reactor being located within the reactor system;

(B) during a first time interval of a second conversion step
  (a) conducting a first-reactant through the first conduit and a second-reactant through the second conduit;
  (b) heating the reactor system by exothermically reacting at least a portion of the second-reactant with (i) at least a portion of the combustible non-volatiles located in the second conduit and (ii) at least a portion of the first-reactant; and (C) during a second time interval of the second conversion step
  (a) conducting at least a portion of the second-reactant through the first conduit; and (b) reacting the second-reactant with at least a portion of the combustible non-volatiles located in the first conduit.

In yet another embodiment, the invention relates to a hydrocarbon conversion process, comprising:
(a) providing a first mixture to a reactor, the first mixture comprising hydrocarbon, wherein (i) the reactor comprises first and second channels and (ii) at least a portion of the hydrocarbon includes alkane;
(b) exposing the first mixture to a temperature ≥800° C. in the reactor and abstracting sufficient heat from the reactor to convert at least a portion of the first mixture's alkane to combustible non-volatiles and unsaturated hydrocarbon;
(c) transferring at least a portion of the unsaturated hydrocarbon away from the reactor via the first and second channels, at least a portion of the combustible non-volatiles being deposited in the first and second channels during the transfer;
(d) exothermically reacting fuel and oxidant in the reactor during a first time interval, the fuel being provided via the first channel and the oxidant being provided via the second channel, in order to
 (i) replace at least a portion of the heat abstracted from the reactor during the conversion and
 (ii) combust at least a portion of the combustible non-volatiles in the second channel; and
(e) providing additional oxidant to the reactor via the first channel during a second time interval in order to combust at least a portion of the combustible non-volatiles in the first channel.

DESCRIPTION

Figure 1:
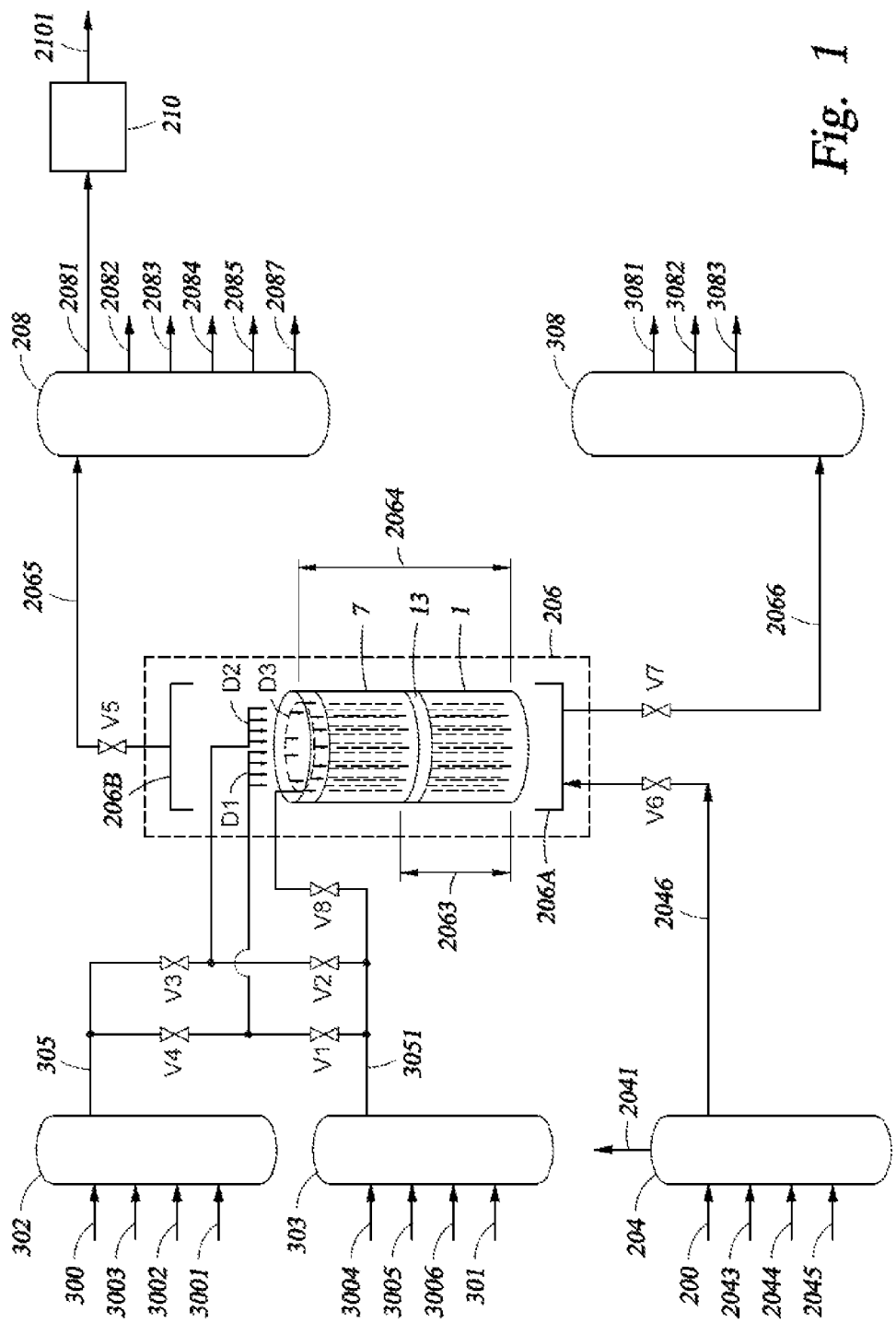
FIG. 1 schematically shows an embodiment of the invention utilizing a reverse-flow pyrolysis reactor system.

Although U.S. Pat. No. 2,845,335 desirably removes coke from at least some of the system's reactors during each of the combustion steps, it has been found that this benefit is obtained at a considerable loss in process efficiency. The Stoichiometry of efficient combustion generally requires a combustion mixture comprising significantly more air (higher volumetric flow rate) than fuel. Since reactors three and four of the conventional process are of similar volume, efficient combustion leads to an air space velocity (GHSV) that is much larger than the fuel GHSV during the conventional process's second and fourth steps. This leads to a thermal imbalance between reactor's three and four because regenerative-bed processes such as heat transfer and heat removal are closely related to space velocity. Should the second and fourth steps be operated at substantially equal air-fuel flow rates, to equalize GHSV and reduce the thermal imbalance, the inefficient combustion conditions would lead to lower temperatures in reactor one and two, which reduces conversion to the desired products.

It has been found that these and other deficiencies in the conventional process can be overcome by utilizing a reactor system comprising first and second regenerative reactors (each reactor being, e.g., a unitary reactor bed). The first reactor comprises at least one first conduit and at least one second conduit. During the oxidation step, (i) the first conduit is a "multi-purpose" conduit, which conveys fuel during a first interval of the oxidation step and oxidant during a second interval of the oxidation step and (ii) the second conduit is an oxidant conduit which conveys oxidant during the oxidation step's first and second intervals. During the pyrolysis step, the first and second conduits convey pyrolysis products in an average flow direction that is the reverse of the average flow of fuel and oxidant. In other words, the process comprises two steps (an oxidation step and a pyrolysis step), with the oxidation step comprising at least two substantially non-overlapping intervals.

Since the first reactor has a conduit (the second conduit) dedicated to the flow of oxidant during both intervals of the oxidation step, (i) the cross-sectional area of the multi-purpose conduit can be appropriately sized for providing the desired oxidant-fuel mixture for combustion during the first interval and (ii) switching the multi-purpose conduit from fuel-flow to oxidant-flow between the first and second intervals can be accomplished without a significant flow-rate change, thereby lessening or even eliminating a thermal imbalance between the conduits during the first and second intervals. Besides increased thermal efficiency, decreased thermal imbalance, and increased yield of desired products over the conventional process, the process of the invention removes coke deposited in the first and second conduits during the oxidation step, thereby obviating the need for a second oxidation step having reversed fuel-air flow, as in the conventional process.

In one embodiment, a first mixture comprising hydrocarbon is provided to the reactor system during the pyrolysis step. The first mixture is pyrolysed, thereby producing a hydrocarbon-containing pyrolysis product, e.g., second mixture comprising $C_2$ unsaturates and combustible non-volatiles, e.g., coke. A portion of the combustible non-volatiles remain in the first and second conduits, e.g., as a deposit. Optionally, a third mixture is derived from the second mixture, e.g., by separating from the second mixture one or more of molecular hydrogen, saturated hydrocarbon, etc. The pyrolysis is endothermic, with at least a portion of the heat utilized by the pyrolysis being provided by the reaction of a fourth mixture in the oxidation step, the fourth mixture comprising first and second reactants. The first reactant comprises fuel, e.g., molecular hydrogen and/or hydrocarbon. The second reactant comprises oxidant, e.g., molecular oxygen. A fifth mixture is produced during the oxidation step, the fifth mixture comprising products derived from oxidation reactions of the fourth mixture, products derived from the oxidation of non-volatiles deposited in the reactor during preceding pyrolysis steps, and any un-reacted fourth mixture. The invention is not limited to methods for converting hydrocarbon to acetylene and/or ethylene. The invention is generally applicable to any process resulting in the conversion of hydrocarbon to coke in a reverse-flow pyrolysis reactor, including those for converting methane under thermal pyrolysis conditions at a temperature $\geq 1.20 \times 10^{3\circ}$ C.

In an embodiment, the first and second conduits each comprise channels within a first reactor, e.g., a first reactor bed. While not wishing to be bound by any theory or model, it is believed that locating the multi-purpose channel and second-reactant channel within a unitary reactor (the first reactor), as is the case in this embodiment, leads to a considerable improvement in the reactor-system's thermal efficiency over the conventional reactor, which locates its first and second conduits in separate reactor beds.

In this embodiment, the oxidation step comprises first and second intervals. During the first interval of the oxidation step, the first reactant is conducted through the first reactor via a multi-purpose channel (a first channel) and at least a first portion of the second reactant is conducted through the first reactor via a second-reactant channel (a second channel). During the second interval, a first portion of the second reactant is conducted through the multipurpose channel, and a second portion of the second reactant is conducted through the second-reactant channel. Optionally, first reactant is conveyed to the reactor system during the oxidation step's second interval, e.g., via (i) a second multi-purpose channel, the second multi-purpose channel being utilized to convey second reactant during the first interval and/or (ii) a first-reactant channel which can be a third channel located in the first reactor, the first-reactant channel being utilized solely for conveying the first reactant during the first and second intervals. It can be desirable to utilize a first-reactant channel in embodiments where (i) conveying the first reactant does not result in the accumulation of a significant amount of non-volatiles in the first-reactant channel and/or (ii) the second mixture is not conveyed through the first-reactant channel during the pyrolysis step. Optionally, the first and second reactants combine downstream of the first reactor to produce the fourth mixture during both the first and second intervals.

The fuel and oxidant components of the fourth mixture exothermically react to form the fifth mixture, thereby heating (and regenerating) the first reactor for the pyrolysis step. The fifth mixture is conducted away via the channel(s) of the second reactor, which increases the second reactor's temperature, thereby regenerating the second reactor for the endothermic pyrolysis step. Optional flow control means, such as valve means, sparger means, and/or distributor means, etc., and combinations thereof can be utilized to direct the first and second reactants and portions thereof to the designated channels during the first and second intervals.

Process objectives will generally dictate the total flow amount (moles, volume, or mass) of first and second reactant passing through the reactor over the course of the oxidation step. This total flow in an oxidation step is carried by the available channels over the available intervals. When a reactant is conveyed through a plurality of channels during an interval, it is understood that each of the channels conveys a portion of the given reactant. Such portions (first, second, etc.) are expressly identified in certain embodiment for clarity, but it should be understood that this description is optional nomenclature.

In another embodiment, the first reactor comprises at least three channels, one second-reactant channel and two multi-purpose channels. During the first interval of the oxidation step, the first multipurpose channel is utilized for transporting the first reactant. The second multi-purpose channel is utilized for conducting a first portion of the second reactant and the second-reactant channel is utilized for conducting a second portion of the second reactant. During the oxidation step's second interval, the second multi-purpose channel is utilized for conducting the first reactant. The second multi-purpose channel is utilized for conducting a first portion of the second reactant and the second-reactant channel is utilized for conducting a second portion of the second reactant. The first portion:second portion weight ratio depends, e.g., on the configuration of the reactor system, and can change from interval-to-interval of the oxidation step. The first multi-purpose channel comprises all the passages within the first reactor that are utilized for transporting the first reactant during the first interval and second reactant during the second interval. The second multi-purpose channel comprises all the passages within the first reactor that are utilized for transporting the second reactant during the first interval and the first reactant during the second interval. The second-reactant channel comprises all the passages within the first reactor that are utilized for transporting second reactant during both the first and second intervals. After the oxidation step, the fifth mixture is conducted away and the first mixture is conducted to the reactor system for the pyrolysis step.

During the pyrolysis step, the first mixture is conducted to the second reactor, wherein the first mixture is pyrolysed under thermal pyrolysis conditions to produce the second mixture. A first portion of the second mixture, e.g., a portion in the vapor phase under the thermal pyrolysis conditions, is conducted away from the reactor system via the channels within the first reactor. A second portion of the second mixture, the second portion comprising $\geq 50.0$ wt. % of the second mixture's combustible non-volatiles (e.g., coke), remains in the channels of the first reactor, e.g., as a deposit. Deriving the second mixture from the first mixture in such a system does not require a catalyst, though one can be used, e.g., to optionally convert light hydrocarbon (e.g., propane) in the first mixture to propylene.

In another embodiment, the process comprises an oxidation step, a pyrolysis step, and a second oxidation step, with the first oxidation step operated as in the first interval of the preceding embodiments and the second oxidation step operated as in the second interval.

Alternating oxidation and pyrolysis steps can be conducted in sequence, e.g., continuously. A feature of the invention is that at least a portion of the combustible non-volatiles deposited in a multi-purpose and second-reactant channels of the first reactor during a pyrolysis step is removed by oxidation during at least one interval of a subsequent oxidation step.

The pyrolysis and oxidation steps of the preceding embodiments can be operated in sequence, e.g., periodically or aperiodically. The process can be operated in batch, semi-continuous, or continuous modes. The duration of the pyrolysis step is substantially independent of the duration of the oxidation steps. The duration of the first and second intervals can be substantially the same, but this is not required. In an embodiment, the reactor system operates, e.g., in series, parallel, or a combination thereof, and utilizes accompanying valve means for conducting the first, second, fourth, and fifth mixtures to/from the reactors of the reactor system. For example, in one embodiment reactor system includes first and second reactors, oriented in a series relationship with each other with respect to a common flow path, optionally along a common axis. The common axis may be horizontal, vertical, or some other orientation with respect to the surface of the earth.

For the purpose of this description and appended claims, the following terms are defined. The term "hydrocarbon" means molecules (and mixtures thereof) including both carbon atoms and hydrogen atoms, and optionally including other atoms (heteroatoms) such as oxygen, sulfur, and nitrogen. The term "oxidant" means a composition (e.g., molecular oxygen) that is capable of oxidizing another composition or part thereof (e.g., hydrocarbon or a hydrocarbon mixture). The term "molecular hydrogen" means $H_2$. The term "molecular oxygen" means $O_2$.

The term "polymer" means a composition including a plurality of macromolecules, the macromolecules containing recurring units derived from one or more monomers. The macromolecules can have different size, molecular architecture, atomic content, etc. The term "polymer" includes macromolecules such as copolymer, terpolymer, etc. The "Periodic Table of the Elements" means the Periodic Chart of the Elements as tabulated on the inside cover of The Merck Index, 12th Edition, Merck & Co., Inc., 1996.

The terms "convert", "conversion", "converting", etc., with respect to pyrolysis processes include, e.g., any molecular decomposition, cracking, breaking apart, reformation of molecules, including hydrocarbon, oxygenate, etc., by at least pyrolysis heat. With respect to non-pyrolysis processes that are at least partly catalytic, the term conversion includes, e.g., hydroprocessing (such as hydrogenation, hydrotreating, etc.), hydroformylation, catalytic separation, etc.

The term "pyrolysis" means an endothermic reaction for converting molecules into (i) atoms and/or (ii) molecules of lesser molecular weight, and optionally (iii) molecules of greater molecular weight, e.g., processes for converting hydrocarbons such as methane, ethane and/or propane to molecular hydrogen and unsaturates such as ethylene, propylene and acetylene.

The terms "reactor", "reactor system", "regenerator", "recuperator", "regenerative bed", "monolith", "honeycomb", "reactant", "fuel", and "oxidant" have the meanings disclosed in U.S. Pat. No. 7,943,808, which is incorporated by reference herein in its entirety. The term "pyrolysis reactor", as used herein, refers to a reactor, or combination or system thereof for converting hydrocarbons by at least pyrolysis. With respect to pyrolysis reactors, the term "residence time" means the average time duration for non-reacting (non-converting by pyrolysis) molecules (such as He, $N_2$, Ar) having a molecular weight in the range of 4 to 40 to traverse a pyrolysis region of a pyrolysis reactor. The term "pyrolysis stage" means at least one pyrolysis reactor, and optionally including means for conducting one or more feeds thereto and/or one or more products away therefrom. With respect to reactors, the term "region" means a location within a reactor, e.g., a specific volume within a reactor, a specific volume between two reactors and/or the combination of different disjointed volumes in one or more reactors. A "pyrolysis region" is a region for conducting pyrolysis. The pyrolysis region can include, e.g., one or more conduits, channels, or passages. The term "conduit" refers to means for conducting a composition from one location to another. The term encompasses (i) elementary conducting means, such as a pipe or tube, and (ii) complex means such as tortuous pathways through conducting means, e.g., pipes, tubes, valves, and reactors, that are filled with random packing. The term "passage" means a geometrically contiguous volume element that can be utilized for conveying a fluid within a reactor, regenerator, recuperator, regenerative bed, monolith, honeycomb, etc. The term "channel" means a plurality of passages that can be utilized together for conveying a fluid within the reactor, regenerator, recuperator, regenerative bed, monolith, honeycomb, etc. For example, a honeycomb monolith can comprise a single channel, the channel having a plurality of passages or sets of passages, e.g., hundreds of thousands of passages per square meter of the honeycomb's cross-section.

The term "thermal pyrolysis" means <50.0% of the heat utilized by the pyrolysis is provided by exothermically reacting the pyrolysis feed, e.g., by exothermically reacting an oxidant with hydrocarbon and/or hydrogen of the first mixture. The term "thermal pyrolysis reactor" means a pyrolysis reactor wherein ≥50.0% of the heat utilized by the pyrolysis is provided by heat transfer from reactor components, e.g., solid surfaces associated with the reactor such as tubulars or bed materials; optionally ≥80.0% or ≥90.0% of the heat utilized by the pyrolysis is provided by such heat transfer. Optionally, an exothermic reaction (e.g., combustion) occurs within the thermal pyrolysis reactor.

The term "high-severity" with respect to the pyrolysis of a feed comprising hydrocarbon, e.g., the first mixture, means pyrolysis operating conditions resulting in the conversion to acetylene of ≥10.0 wt. % of the feed's hydrocarbon based on the total weight of hydrocarbon in the feed. The operating conditions for a thermal pyrolysis reactor may be characterized by a severity threshold temperature that divides low-severity operating conditions in thermal pyrolysis reactors from high-severity operating conditions in thermal pyrolysis reactors. The severity threshold temperature is defined as the lowest temperature at which the feed to the reactor may react at a residence time ≤0.1 second to make at least 10.0 wt. % acetylene as a percent of the hydrocarbons in the mixture evaluated at the given operating conditions of the process. The high-severity operating conditions for a thermal pyrolysis reactor may be characterized as peak pyrolysis gas temperatures that are greater than the severity threshold temperature. The low-severity thermal pyrolysis reactor may be characterized as pyrolysis gas temperatures that are less than the severity threshold temperature and no pyrolysis gas temperatures that exceed the severity threshold temperature. For example, for the thermal conversion of a methane feed at a pressure of 14.7 psig (101 kPa) and with 2:1 molar ratio of molecular hydrogen to methane, the threshold temperature is about 1274° C. for this process. At temperatures at or above 1274° C., yields of acetylene can exceed 10.0 wt. % of feed hydrocarbon, at some time ≤0.1 seconds. Conversely, at temperatures below 1274° C., there are no times ≤0.1 seconds for which yields of acetylene reach 10.0 wt. % of the methane.

The term "peak pyrolysis gas temperature" means the maximum temperature achieved by the bulk pyrolysis stream gases as they travel through the pyrolysis reactor (e.g., cracking region or radiant region). One skilled in the art will appreciate that temperatures immediately proximate to a partition may be higher, and may, in some infinitesimal boundary layer, actually approach the solid temperature. However, the pyrolysis temperature referred to herein should be considered a bulk gas temperature, which is a temperature that could be measured by a device (such as a thermocouple) that is not in contact with the solid material. For example, if the gas is traveling through tubulars in a thermal pyrolysis reactor, the bulk gas temperature may be taken as the average temperature over any tubular cross-section, and the peak pyrolysis gas temperature as the highest cross-sectional-average temperature of the pyrolysis stream.

In an embodiment, a second mixture is derived by pyrolysis of a first mixture, the first mixture being derived from one or more source materials. The term "source materials" means sources comprising hydrocarbon. Examples of source materials comprising hydrocarbon include one or more of hydrocarbon derived from petroleum; syngas (a mixture comprising carbon monoxide and hydrogen); methane; methane-containing streams, such as coal bed methane, biogas, associated gas, natural gas, and mixtures or components thereof; synthetic crudes; shale oils; or hydrocarbon streams derived from plant or animal matter. Suitable hydrocarbon source materials include those described in U.S. Pat. Nos. 7,943,808 and 7,544,852, which are incorporated by reference herein in their entirety.

The term "hydrogen content" of a mixture or source material means atomic hydrogen bound to carbon and/or heteroatoms covalently bound thereto and which excludes molecular hydrogen ($H_2$) in the mixture (or source material) expressed as a weight percent based on the weight of the hydrocarbons in the mixture (or source material). Optionally, one or more mixtures and/or source materials comprises non-volatiles. The term "non-volatiles" means molecules and mixtures thereof having a nominal atmospheric boiling point $\geq 570.0°$ C., e.g., refractory oxygenates, refractory hydrocarbon, metals, minerals, etc. American Society of Testing and Materials ("ASTM") methods can be used to determine the nominal atmospheric boiling point (ASTM method 1078) and the amount and properties of such non-volatiles, such as ASTM methods D-6560, D-7061, D-189, D-482, D-524, and D-2415. Non-volatiles that are capable of being combusted are called "combustible non-volatiles". The term non-volatiles encompasses, e.g., coke, ash, soot, resid, metal, mineral, ash, ash-forming asphaltenic, tar, etc., including those formed, e.g., during or after oxidation (e.g., combustion or partial oxidation) and/or pyrolysis, including those which may remain as a residue or deposit in the reaction region. Optionally, one or more mixtures and/or source materials comprises $C_{3+}$. The term "$C_{3+}$" means molecules having at least three carbon atoms, including, e.g., coke and soot, whether those products emerge from the reactor or remain within the pyrolysis reactor. The term "reactor effluent" means products of pyrolysis conducted away from the reactor. The reactor effluent comprises $C_2$ unsaturates, where the term "$C_2$ unsaturates" means hydrocarbon having two carbon atoms and two or four hydrogen atoms. The first, second, third, fourth, and fifth mixtures, and related products and byproducts will now be described in more detail.

I. First Mixture

In an embodiment, the first mixture comprises hydrocarbon and optionally further comprises molecular hydrogen and/or diluent. The type of hydrocarbon is not critical; e.g., the hydrocarbon can even compromise hydrocarbon non-volatiles, including those that are not in the gas phase at the temperature, pressure, and composition conditions subsisting at the inlet to the pyrolysis reactor. The first mixture's hydrocarbon includes alkane. The alkane can be, e.g., normal and/or isoalkane, including mixtures thereof. Optionally, the first mixture comprises $\geq 10.0$ wt. % alkane based on the weight of the first mixture, e.g., $\geq 25.0$ wt. %, such as $\geq 50.0$ wt. %.

In an embodiment, the hydrocarbon is derived from one or more source materials, as defined in the preceding section. The first mixture can be derived from the source material(s) located upstream of the pyrolysis, but this is not required. For example, in one embodiment hydrocarbon derived from a first source material and hydrogen derived from a second source material are conducted separately to the pyrolysis reactor, the hydrocarbon and hydrogen being combined to produce the first mixture proximate to (e.g., within) the pyrolysis reactor. Optionally, the hydrocarbon has (or is derived from one or more source materials having), e.g., a hydrogen content in the range of 6.0 wt. % to 25.0 wt. %, 8.0 wt. % to 20.0 wt. % (e.g., not natural gas), or 20.0 wt. % to 25.0 wt. % (e.g., natural gas). In a particular embodiment, the hydrocarbon of the first mixture is derived from natural gas (e.g., a methane-containing gas of synthetic and/or geological origin). The first mixture can comprise, e.g., upgraded natural gas (such as natural gas that has been sweetened and/or dehydrated). Besides methane, natural gas commonly includes other hydrocarbons (such as ethane and other alkanes), generally in amounts greater than or equal to the amount of methane in the natural gas on a weight basis. Optionally, the natural gas further comprises diluent, e.g., one or more of hydrogen sulfide, nitrogen or oxygenate such as water, $CO_2$, etc. which can be used as a diluent source when diluent is present in the first mixture.

Optionally, the first mixture further comprises diluent, e.g., $\geq 1.0$ wt. % of diluent based on the weight of the first mixture. Suitable diluents (which can be a diluent mixture) include one or more of molecular hydrogen, oxygenate, such as water, nitrogen ($N_2$), hydrogen sulfide, $C_{4+}$ mercaptans, amines, mixtures of amines, non-hydrocarbon non-volatiles (whether combustible or not) including refractory inorganics, such as refractory oxygenates, inert gas (including inert gas mixtures), etc. In an embodiment, the first mixture comprises $\leq 10.0$ wt. % diluent. When the first mixture further comprises a molecular hydrogen diluent, the first mixture can have a molecular hydrogen to carbon (as all carbon atoms in the first mixture that are not bound to oxygen atoms, e.g., as can be determined by Nuclear Magnetic Resonance Spectroscopy) molar ratio in the range of from 0.0 to 5.0, e.g., 0.1 to 4.0, such as 1.0 to 3.0 or 1.0 to 2.0. Optionally, the first mixture has a hydrogen (all hydrogen atoms in the first mixture regardless of atomic or molecular form) to carbon (all carbon atoms in the first mixture regardless of atomic or molecular form) atomic ratio in the range of from 1.0 to 15.0, e.g., in the range of from 3.0 to 8.0.

In an embodiment, the first mixture comprises a total amount of non-combustible non-volatiles (e.g., ash; ASTM D-189), from all sources, $\leq 2.0$ parts per million weight (ppmw) based on the weight of the first mixture, e.g., $\leq 1.0$ ppmw. Optionally, the first mixture comprises a total amount of combustible non-volatiles (e.g., tar, asphaltenes, ASTM D-6560) in the first mixture, from all sources, $\leq 5$ wt. % based on the weight of the first of the hydrocarbon in the first mixture, e.g., $\leq 1.0$ wt. %, such as $\leq 100.0$ ppmw or $\leq 10.0$ ppmw, provided the presence of the combustible non-volatiles does not result in $\geq 2.0$ ppmw (e.g., $\geq 1.0$ ppmw) based on the weight of the second mixture.

In an embodiment, the first mixture has one or more of the following properties: (i) at least 15.0 wt. % of the molecular hydrogen in the first mixture (based on the total weight of molecular hydrogen in the first mixture) is molecular hydrogen derived from the second mixture or one or more products thereof. In another embodiment, the first mixture comprises $\geq 50.0$ ppm sulfur based on the weight of the first mixture.

In an embodiment, the first mixture has the following composition: (a) the first mixture comprises (i) $\geq 10.0$ wt. % of hydrocarbon, e.g., $\geq 25.0$ wt. % hydrocarbon and (ii) $\geq 1.0$ wt. % molecular hydrogen, e.g., $\geq 15.0$ wt. % molecular hydrogen, the weight percents being based on the weight of the first mixture and/or (b) the first mixture comprises (i) ≥0.10 mole % of hydrocarbon, e.g., in the range of 0.10 mole % to 90.0 mole % and (ii) ≥0.01 mole % of molecular hydrogen, e.g., in the range of 0.01 mole % to 90.0 mole %, the mole percents being per mole of the first mixture.

II. Second Mixture

In an embodiment, the second mixture comprises ≥1.0 wt. % of unsaturates and ≥1.0 wt. % of combustible non-volatiles, based on the weight of the second mixture. Optionally, the second mixture further comprises one or more of hydrogen, methane, ethane, or diluent, and optionally further comprises benzene, paraffin (iso-, cyclo-, and/or normal) having ≥3 carbon atoms, etc.

In an embodiment, ≥90.0 wt. %, e.g., ≥95.0 wt. %, such as ≥99.0 wt. % of the second mixture's combustible non-volatiles remain in the regenerative, reverse-flow pyrolysis reactor, e.g., as a deposit in the channels of the first and/or second reactor, the weight percents being based on the weight of the combustible non-volatiles in the second mixture. In an embodiment, the second mixture has a $C_{3+}$ hydrocarbon:$C_2$ unsaturates weight ratio ≤about 1.0, e.g., ≤about 0.4. Optionally, the second mixture has a combustible, non-volatiles:olefin weight ratio ≤about 1.0, e.g., ≤about 0.4, such as ≤about 0.1.

In an embodiment, a third mixture is derived from the second mixture in one or more upgrading/treatment stages, e.g., by separating from the second mixture one or more of hydrogen, methane, and/or combustible non-volatiles. In another embodiment, the third mixture comprises, consists essentially of, or consists of the second mixture, e.g., that part of the second mixture which is in the vapor phase at the downstream end of a regenerative, reverse-flow pyrolysis reactor. For example, a third mixture comprising acetylene can be separated from the second mixture. If desired, at least a portion of the third mixture's acetylene can be converted to ethylene, and at least portion of the ethylene can be polymerized, e.g., to produce polyethylene.

III. Fourth Mixture

The fourth mixture comprises first and second reactants. In an embodiment, the first reactant comprises fuel and the second reactant comprises oxidant. The fuel and oxidant can be the same as those disclosed in U.S. Pat. No. 7,943,808. Optionally, the fuel is derived from, comprises, consists essentially of, or consists of one or more of hydrogen, CO, methane, methane containing streams, such as coal bed methane, biogas, associated gas, natural gas and mixtures or components thereof, etc. Exothermically reacting the first reactant's fuel component and the second reactant's oxidant component provides at least a portion of the heat utilized by the pyrolysis, e.g., ≥50%, such as ≥75%, or ≥95% of the heat utilized by the pyrolysis. Additional heat, when needed, can be provided to the regenerative, reverse-flow pyrolysis reactor by, e.g., a burner or furnace, e.g., a furnace external to the reactor, but in thermal communication therewith. The first and second reactants mix within the regenerative, reverse-flow pyrolysis reactor to produce the fourth mixture, the fuel and oxidant then reacting, e.g., by an oxidation reaction such as combustion, as the fourth mixture traverses at least a portion of the pyrolysis reactor. The first reactant comprises fuel, e.g., molecular hydrogen, synthesis gas (mixtures of CO and $H_2$), or hydrocarbon, such as ≥10.0 wt. % hydrocarbon (including mixtures thereof), or ≥50.0 wt. % hydrocarbon, or ≥90.0 wt. % hydrocarbon based on the weight of the first reactant. The second reactant comprises oxidant, e.g., molecular oxygen.

The amount of oxidant in the second reactant and the relative amounts of first and second reactants utilized to produce the fourth mixture can be specified in terms of the amount of oxidant in the second reactant needed for oxidizing combustible non-volatiles in the reactor system ("X") and the amount needed for the substantially stoichiometric oxidation of the first reactant's fuel component ("Y"). In an embodiment, the total amount of oxidant in the fourth mixture is Z(X+Y), wherein Z is in the range of 0.8 to 10.0, e.g., in the range of 1.0 to 3.0, and the amounts X and Y are on a molar basis. When Z>1.0, the excess oxidant can be utilized, e.g., for moderating the reaction temperature during the oxidation step as disclosed in U.S. Pat. No. 7,943,808, and/or for conveying heat within the reactor system. In certain embodiments, it is desirable for the total flow amount to remain at a relatively constant flow rate over the duration of the oxidation step's intervals. In such cases the proportion of first or second reactant flowing in a given interval will be roughly proportional to the duration of that interval (rate×time=amount).

The fourth mixture is generally produced in a mixing region, the mixing region being located downstream of the first reactor's channels. The fourth mixture is defined as the combination of the first reactant and second reactant. However, at the point at which these streams combine, the combined stream optionally includes species resulting from the oxidation of combustible non-volatiles located in the first reactor's channels. Optionally, the combined stream further comprises species resulting from reaction of the first and second reactants in one or more of the first reactor's channels, or locations upstream thereof, as a result of comingling of the first and second reactants. Generally, the amount of comingling is small, as disclosed in U.S. Pat. No. 7,943,808. It can be beneficial for the amount of oxidant in the fourth mixture to exceed that needed to oxidize substantially all of the fourth mixture's fuel component, e.g., for (i) oxidizing combustible non-volatiles located in regions of the reactor system downstream of the first reactor's channels, (ii) moderating the temperature during the oxidation of the fourth mixture's fuel component, and/or (iii) transferring heat within regions of the reactor system downstream of the mixing region. The desired amount of excess oxygen can be provided by increasing the relative amount of oxidant in the second reactant and/or by increasing the relative amount of second reactant in the fourth mixture.

Optionally, the fourth mixture further comprises diluent, e.g., ≥1.0 wt. % of diluent based on the weight of the fourth mixture. Suitable diluents (which can be a diluent mixture) include one or more of, e.g., oxygenate (water, carbon dioxide, etc.), non-combustible species, such as molecular nitrogen ($N_2$), and fuel impurities, such as hydrogen sulfide. In an embodiment, the fourth mixture comprises ≤96.0 wt. % diluent, e.g., in the range of 50.0 wt. % to 95.0 wt. % diluent, based on the weight of the fourth mixture. In an embodiment, diluent is provided to the fourth mixture as a component of the second reactant. For example, the second reactant can comprise 60.0 mole % to 95.0 mole % diluent and 5.0 mole % to 30.0 mole % oxidant per mole of the second reactant, such as when the second reactant is air. Optionally, the second reactant has a mass ratio of diluent to oxidant in the range of 0.5 to 20.0, e.g., in the range of 4.0 to 12.0. It can be beneficial for the second reactant (and fourth mixture) to further comprise diluent, e.g., for (i) moderating the temperature during the oxidation of the fourth mixture's fuel component and/or transferring heat within the reactor system.

In an embodiment, the first reactant comprises ≥90.0 wt. % molecular hydrogen based on the weight of the first reactant and the second reactant comprises ≥90.0 wt. % air based on the weight of the second reactant. When the second reactant comprises ≥90.0 wt. % air based on the weight of the second reactant, a fourth mixture produced from these can comprise, e.g., ≥1.0 wt. % molecular oxygen, e.g., in the range of 5.0 wt. % to 25.0 wt. %, such as 7.0 wt. % to 15.0 wt. %; ≥0.1 wt. % fuel, e.g., in the range of 0.2 wt. % to 5.0 wt. %, the weight percents being based on the weight of the fourth mixture, with the balance of the fourth mixture being molecular nitrogen diluent, e.g., ≥50.0 wt. % diluent, such as in the range of 60.0 wt. % to 94.50 wt. % diluent based on the weight of the fourth mixture.

IV. Fifth Mixture

The fifth mixture comprises (i) products derived from the exothermic reaction of the fourth mixture's fuel and oxidant with each other and with the combustible non-volatiles within the reactor, optionally (ii) diluent, when diluent is present in the fourth mixture, and/or (iii) unreacted fuel and oxidant. When the exothermic reaction of the fuel and oxidant involves hydrocarbon combustion, or when a diluent is present in the fourth mixture (such as $N_2$ or $H_2S$), the fifth mixture can comprise carbon dioxide, and can further comprise sulfur oxides, nitrogen oxides, etc.

A continuous or semi-continuous process for deriving (a) the second mixture from the first mixture and (b) the fifth mixture from the fourth mixture in a regenerative, reverse-flow reactor system will now be described in more detail. Although the process is described in terms of a particular regenerative, reverse-flow thermal pyrolysis reactor having first and second reactors the invention is not limited thereto, and this description is not meant to foreclose other embodiments within the broader scope of the invention.

V. Operation in a Regenerative, Reverse-Flow Reactor

Figure 2:
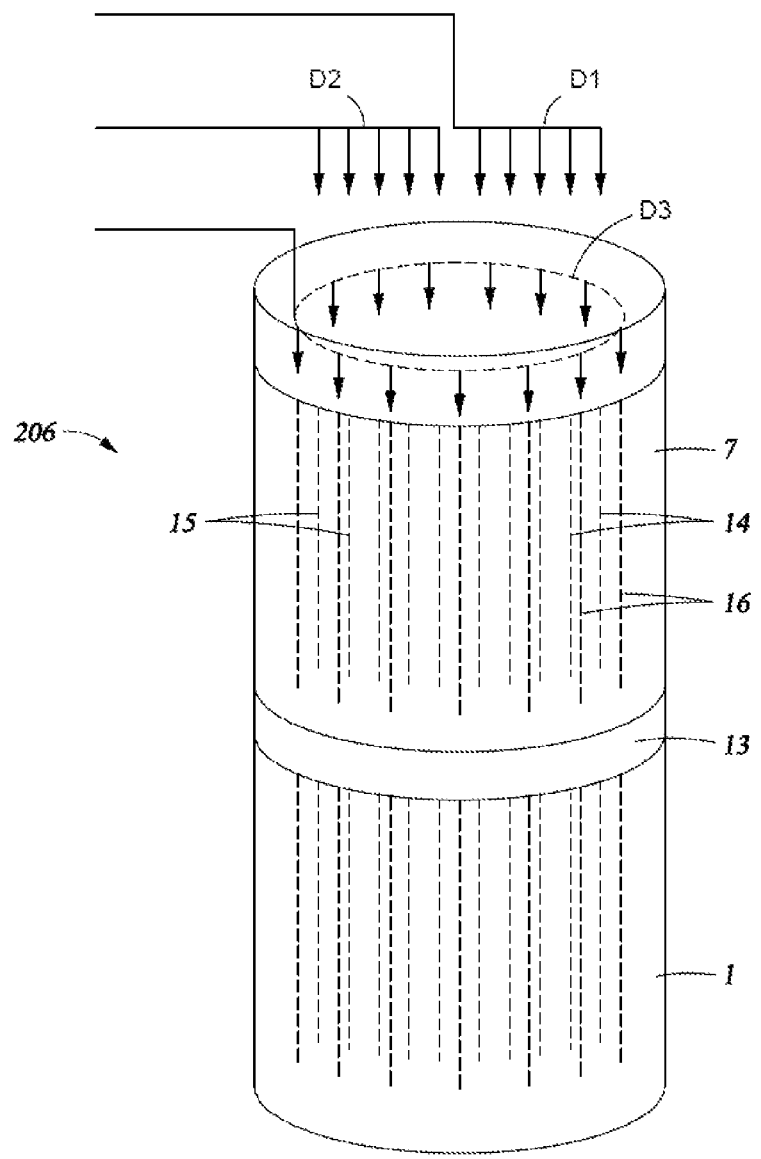
FIG. 2 schematically shows a reverse-flow pyrolysis reactor useful in the system of FIG. 1.

One embodiment of the invention is illustrated in FIGS. 1 and 2. This embodiment relates to a hydrocarbon conversion system and process, comprising pyrolysing a first mixture comprising hydrocarbon under thermal pyrolysis conditions to produce a second mixture comprising unsaturated hydrocarbon and combustible non-volatiles. For example, when the first mixture comprises methane, the thermal pyrolysis conditions can include, e.g., exposing the first mixture to a temperature $\geq 1.20 \times 10^{3 \circ}$ C., e.g., $\geq 1.40 \times 10^{3 \circ}$ C., at a total pressure ≥0.1 bar (absolute). The pyrolysis is conducted in a first region 2064 of at least one regenerative, reverse-flow pyrolysis reactor in pyrolysis stage 206. The process for deriving the second mixture from the first mixture is generally endothermic, and can be conducted, e.g., under low or high-severity thermal pyrolysis conditions. The process further comprises exothermically reacting in a second region 2063 at least a portion of a second reactant with one or more of (i) a first reactant or (ii) combustible non-volatiles that may be present in stage 206 during the oxidation step, the products of (i) and/or (ii) comprising a fifth mixture that can be conducted away.

Figure 3:
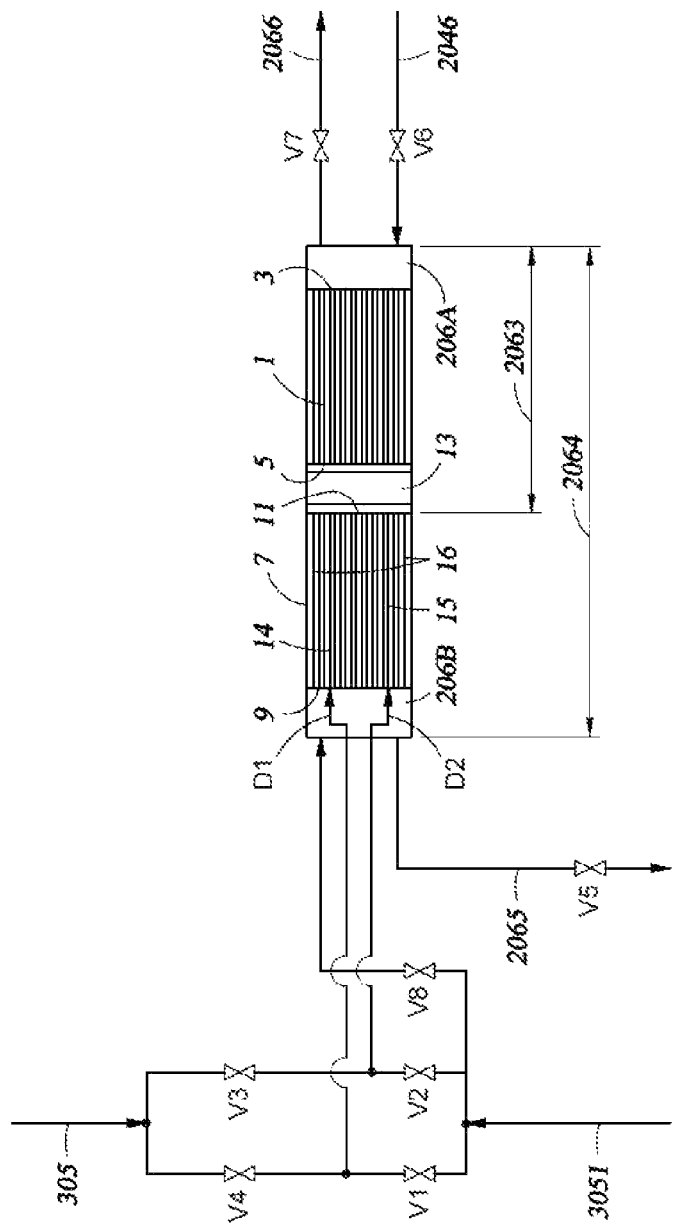
FIG. 3 schematically shows another reverse-flow pyrolysis reactor useful in the system of FIG. 1. The reactor includes a plenum that is useful for directing the flow of oxidant to the reactor and valve means that are useful for controlling the flow of gasses to and from the reactor.

A particular embodiment is shown in FIG. 3, with plenum 206B substituting for distributor D3. In the embodiment of FIG. 3, the exothermic reaction region 2063 can be located, e.g., between a first point proximate to the downstream end 11 of first reactor 7 and a second point proximate to the downstream end 3 of second reactor 1; "downstream" in this case being with respect to the average flow of the fourth mixture. The pyrolysis region 2064 can be located, e.g., between a first point proximate to the upstream end 3 of the second reactor 1 and a second point proximate to the downstream end 9 of first reactor 7, "upstream" and "downstream" now being with respect to the average flow of the first mixture. It should be appreciated that the invention can be practiced without precisely defining (a) the boundaries of regions 2063 and 2064. Although region 2063 (the exothermic reaction region) is at least partially coextensive with pyrolysis region 2064, the upstream end of region 2063 ("upstream" with respect to the average flow of the fourth mixture) is generally proximate to the location where a significant amount of the first and second reactants combine to produce an exothermic reaction. The downstream (with respect to the average flow of the first mixture) end of region 2063 is generally proximate to the downstream end of second reactor 1 as shown in FIG. 3, though this is not required, and in at least one embodiment the downstream end of region 2063 is located further downstream, e.g., in conduit 2066.

The exothermic reacting of the second reactant with (i) the first reactant and/or (ii) combustible non-volatiles located in stage 206 during the oxidation step can provide, e.g., ≥50.0% of the heat utilized in the first region for deriving the second mixture from the first mixture. For example, in one embodiment the exothermic reacting of the fourth mixture's fuel and oxidant components provides ≥50.0% of the heat utilized in the first region for deriving the second mixture from the first mixture. The first and second regions can be at least partially coextensive, for example, and the exothermic reacting of the fourth mixture's fuel and oxidant can be conducted at a substantially different time than the pyrolysis. The invention will now be described in terms of the high-temperature thermal pyrolysis of a first mixture to produce a second mixture comprising $C_2$ unsaturates and combustible non-volatiles in a particular regenerative, reverse-flow thermal pyrolysis reactor. The invention is not limited to this embodiment, and this description is not meant to foreclose other embodiments within the broader scope of the invention, e.g., embodiments for producing unsaturated hydrocarbon by steam cracking and/or alkane (e.g., propane) dehydrogenation.

The first mixture can be derived from one or more source materials 200, e.g., natural gas, petroleum, etc., as described in Section I. Optionally, one or more of the source materials are upgraded in optional preparation stage 204 to produce the first mixture. When preparation stage 204 is not utilized, the first mixture can comprise (or consist essentially of, or even consist of) hydrocarbon obtained directly from source materials 200, such as natural gas, e.g., with no intervening process steps. Following the optional preparation stage 204, the first mixture is conducted to the pyrolysis stage 206 wherein it is exposed to a temperature $\geq 1.20 \times 10^{3 \circ}$ C. under thermal pyrolysis conditions, e.g., high-severity, thermal pyrolysis conditions, to convert at least a portion of the first mixture to the second mixture comprising ≥1.0 wt. % of unsaturates and ≥1.0 wt. % of combustible non-volatiles based on the weight of the second mixture. A first portion of the second mixture, e.g., a vapor-phase portion which comprises unsaturates, hydrogen, and saturated hydrocarbon, is conducted away from the pyrolysis stage to an optional upgrading stage 208 for, e.g., separation of a first separated portion. A second portion of the second mixture (comprising combustible non-volatiles) remains in the stage 206, e.g., as a deposit in the pyrolysis reactor. The first portion:second portion weight ratio is ≥1.0, e.g., in the range of 2 to 1000, such as 3 to 100.

The fourth mixture comprises first and second reactants, as specified in Section III. The first reactant can be derived from at least one source material 300, e.g., natural gas, petroleum, other hydrocarbon, etc., including fractions, products, or byproducts thereof. The second reactant can comprise, e.g., oxygen, etc., and can be derived, e.g., from source material 301, such as air. Optionally, the source materials 300 and 301 are upgraded in preparation stages 302 and 303 as shown, to produce the first and second reactants. The first reactant is conducted to stage 206 via conduit 305, the second reactant being conducted via conduit 3051. Stages 302 and 303, when used, can produce the first and second reactants by one or more of separation, conversion, addition of recycled portions of the second and/or fifth mixtures ("EGR"), etc., as described in U.S. Pat. No. 7,943,808.

Figure 2A:
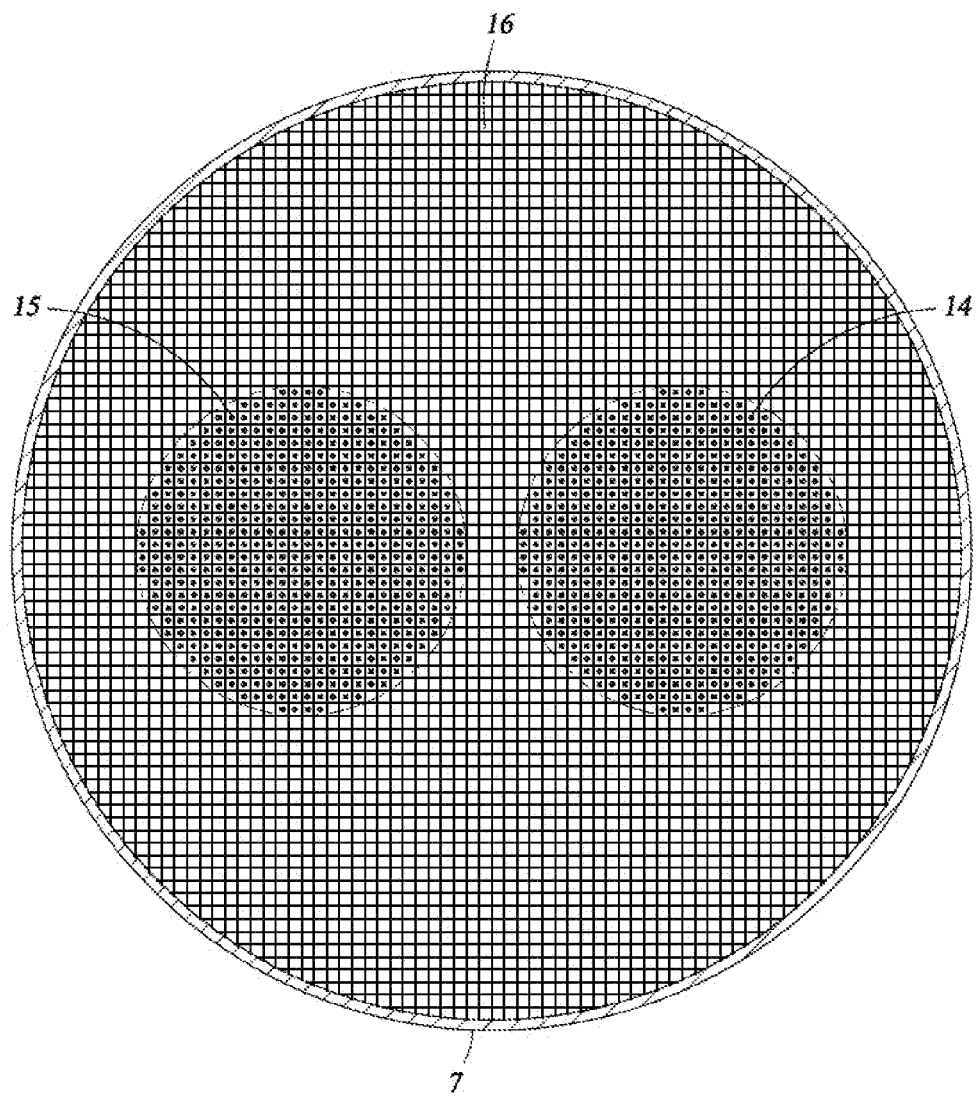
FIG. 2A schematically shows a top view of the reverse-flow pyrolysis reactor of FIG. 2.
Figure 3A:
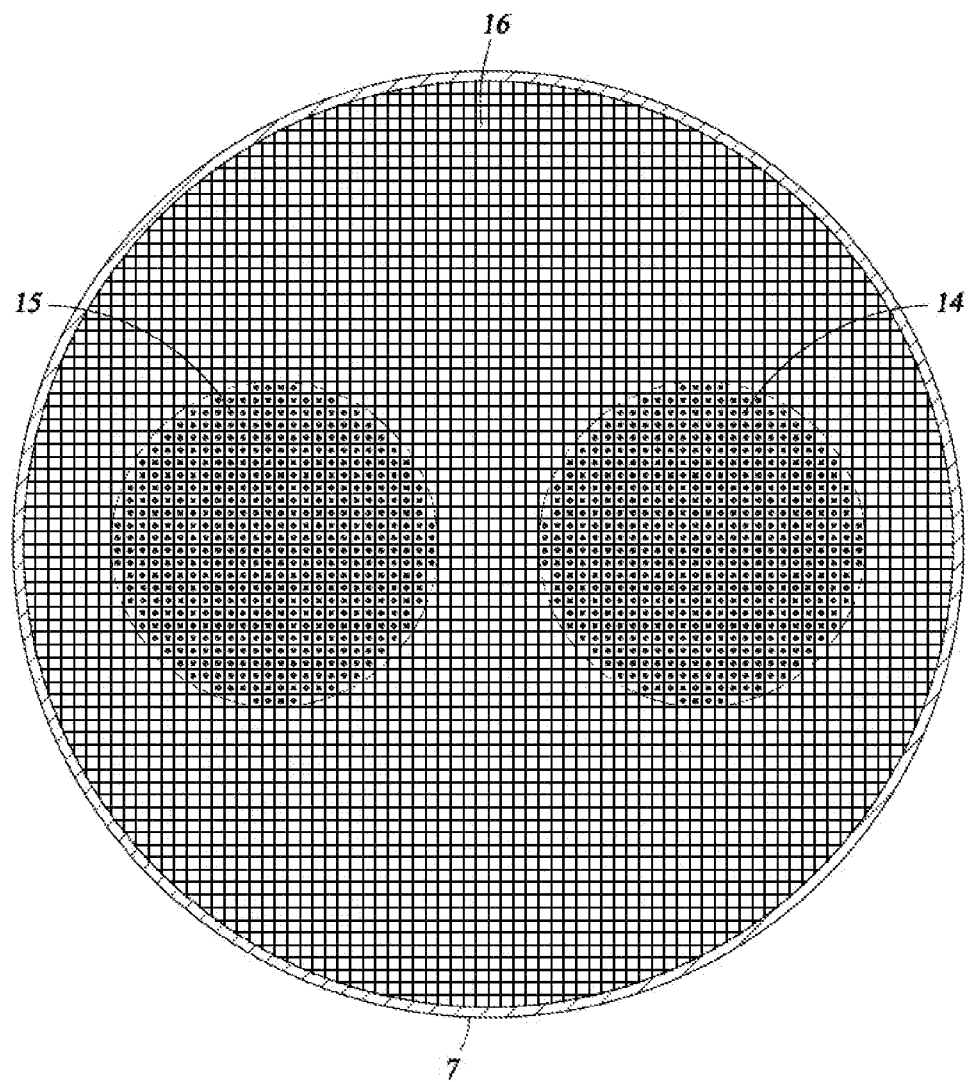
FIG. 3A schematically shows a top view of the reactor of FIG. 3. Utilizing a plenum allows a greater separation of Channels 14 and 15 compared to the reactor of FIGS. 2 and 2A.

The process comprises oxidation and pyrolysis steps carried out in pyrolysis stage 206 having at least one regenerative, reverse-flow pyrolysis reactor. Representative reactor systems are illustrated schematically in FIG. 2 and FIG. 3. The reactors are similar, except that the function of distributor D3 in FIG. 2 is performed by plenum 206B in FIG. 3. End views of reactor 7 are shown in FIGS. 2A and 3A, with the shaded regions representing the approximate locations of distributors D1 and D2, which are utilized to direct reactants into the multi-purpose channels. In both cases, the reactor system comprises at least one first reactor 7 and at least one second reactor 1. The first reactor 7 comprises a first multi-purpose channel 14, a second multi-purpose channel 15, and a second-reactant channel 16. Channel 14 comprises the set of passages identified by the reference number 14 in the figures. Likewise, channel 15 comprises the set of passages identified by the reference number 15 and channel 16 is identified by the set of passages identified by the reference number 16. The second reactor 1 comprises at least one passage. The channels of the first and second reactor can each comprise one or more passages, e.g., a set of passages. In this embodiment, the regenerative, reverse-flow pyrolysis reactor is (i) "reverse flow" in the sense that upstream region of the reactor with respect to the average flow of the first mixture is the downstream region with respect to the average flow of the fourth mixture and (ii) "regenerative" in the sense that at least a portion of the heat consumed during the conversion of the first mixture is provided by exothermically reacting the fourth mixture.

Pyrolysis Step

During the pyrolysis step, valves V1-V4 and V7-V8 are closed. Valves V5 and V6 are open. The first mixture is conducted to the first region (the pyrolysis region) 2064 of the regenerative, reverse-flow pyrolysis reactor via at least one conduit 2046. The second mixture, derived from the first mixture by the pyrolysis, is conducted away from region 2064 via at least one conduit 2065. The reactor optionally includes means for directing the first mixture from conduit 2046 into the passages of the second reactor 1, e.g., plenum 206A and means (such as plenum 206B) for directing at least a portion of the second mixture, e.g., the portion in the vapor phase, to conduit 2065.

In the illustrative embodiment, regions 2063 and 2064 are at least partially coextensive as shown in FIG. 1. Region 2063 encompasses at least the second reactor. Region 2064 encompasses at least a portion of each of the first and second reactors. At least a portion of the heat produced in region 2063 during the exothermic reaction of the fourth mixture during the first and second intervals of the oxidation step is used to provide at least a portion of the heat utilized in region 2064 for the endothermic pyrolysis step. Optionally, a major amount (e.g., >50%) of the heat abstraction occurs in the portion of region 2064 that is coextensive with region 2063.

In an embodiment, the pyrolysis is a high severity pyrolysis and the second mixture comprises acetylene that can be converted, e.g., to ethylene. For example, a third mixture can be derived from at least a portion of the second mixture in optional upgrading stage 208, with the third mixture being conducted via at least one conduit 2086 to a conversion stage 210, for converting at least a portion of the third mixture's acetylene to a first product comprising, e.g., one or more of ethylene, ethylene glycol, acetic acid, acrylic acid, benzene, toluene, or xylene, styrene, or butadiene. Polymerizing at least a portion of the first product, e.g., to produce polyethylene, is within the scope of the invention.

In one embodiment, stage 208 includes upgrading means, e.g., means for removing from the second mixture one or more of hydrocarbon (such as saturated hydrocarbon and/or those containing one or more heteroatoms), diluent, non-volatiles, and hydrogen, etc. For example, stage 208 can include one or more of a tar and/or solid removal means, compression means, adsorption means, distillation means, washing means, or drying means. While stage 208 can encompass conventional processing, e.g., conventional separation means, such as those described in U.S. Pat. No. 7,943,808, the invention is not limited thereto. Separation means can be used, e.g., for removing from the second mixture one or more of condensable species (e.g., condensable hydrocarbon); light-gas (e.g., one or more of hydrogen, light saturated hydrocarbon such as methane, carbon dioxide, hydrogen sulfide, etc.); or water.

Stage 208 can include, e.g., means for cooling and then compressing the second mixture conducted away from stage 206. For example, in embodiments where stage 206 has an outlet pressure <the inlet pressure of the converter of stage 210, stage 208 can include, e.g., compressing at least the portion of the second mixture from which the third mixture is derived in order to achieve the desired stage 210 inlet pressure. Should the second mixture comprise acid gases (e.g., $CO_2$ and/or $H_2S$), these can be removed, e.g., downstream of the compression—a desirable location since the gas volume has been reduced significantly during compression. Conventional methods are suitable for removing acid gases, e.g., caustic treatment, but the invention is not limited thereto. Acid gases separated from the second mixture can be conducted away, e.g., for storage or further processing such as in a Claus plant.

In an embodiment, at least a portion of any hydrogen, saturated hydrocarbon, diluent, etc., separated from unsaturates in upgrading stage 208 are recycled, e.g., by combining such separated species with one or more of the first mixture's source materials, e.g., in preparation stage 204. The pyrolysis will now be described in more detail.

Although the invention is not limited thereto, conventional pyrolysis reactors can be adapted for use in stage 206. Suitable reactors include, for example, regenerative reverse flow reactors as described in U.S. Patent App. Pub. No. 2007/0191664 and thermal pyrolysis reactors as described in U.S. Pat. No. 7,491,250; U.S. patent application Ser. No. 61/349,464; and U.S. Patent App. Pub. Nos. 2007/0144940 and 2008/0142409, all of which are incorporated by reference herein in their entirety. In an embodiment, the thermal pyrolysis is conducted under high-severity thermal pyrolysis conditions, e.g., by exposing the first mixture to temperature in the range of about $1.40 \times 10^3$° C. to about $2.30 \times 10^3$° C., e.g., in the range of about $1.45 \times 10^3$° C. to about $1.80 \times 10^3$° C. Optionally, ≥25.0 wt. % (such as of the ≥50.0 wt. % or ≥75.0 wt. %) of the first mixture achieves a peak pyrolysis gas temperature ≥$1.40 \times 10^3$° C., e.g., in the range of about $1.50 \times 10^3$° C. to about $1.675 \times 10^3$° C., based on the weight of the first mixture.

Although the process is robust and can operate within a wide range of pyrolysis conditions, e.g., temperature, pressure, residence times, severity, etc., the conditions are generally selected to increase the relative amount of $C_2$ unsaturates in the second mixture, e.g., to increase the acetylene to combustible non-volatiles weight ratio. Relatively long residence times can result in over-cracking of the feed molecules, leading to an undesirable increase in the amount of methane and/or combustible non-volatiles in the second mixture. In an embodiment, residence time is ≤about 0.3 seconds, e.g., ≤0.05 seconds. In an embodiment, the pyrolysis is high-severity, thermal pyrolysis and the residence time is ≤0.05 seconds, such as ≤0.02 seconds. Residence time can be selected, e.g., for optimum unsaturates' yield under pyrolysis conditions. This can be done by measuring the amount of unsaturates in the second mixture under substantially constant thermal pyrolysis conditions at a plurality of residence times. The optimum residence time can be approximated using conventional interpolation and extrapolation of the measured values. The optimum residence time can also be approximated using pyrolysis reaction simulations of second mixture composition as a function of pyrolysis conditions and residence time, including conventional pyrolysis reaction simulations.

In an embodiment, the pyrolysis is conducted for a time duration ($t_1$) sufficient for exposing ≥50.0 wt. %, e.g., ≥75.0 wt. %, such as ≥90.0 wt. % of the first mixture (based on the weight of the first mixture) to pyrolysis conditions for a residence time ≤about 0.3 seconds, e.g., ≤0.05 seconds. In an embodiment, $t_1$ is ≤10.0 seconds, e.g., ≤5.0 seconds, such as ≤1.0 seconds. Optionally, $t_1$ is in the range of 0.1 seconds to 100.0 seconds, e.g., 1 to 30 seconds.

Oxidation Step

During the first interval of the oxidation step, valves V8, V7, V2 and V4 are open. Valves V1, V3, V5, and V6 are closed. The first reactant is conducted through at least one conduit 305 and to at least one first distributor (D1), wherein D1 directs the flow of the fuel into channel 14 within first reactor 7. A first portion of the second reactant is conducted through at least one conduit 3051 and to at least one second distributor (D2), wherein D2 directs the flow of the first portion of the second reactant to channel 15 within first reactor 7. A second portion of the second reactant is conducted to the first reactor from conduit 3051, optionally through third distributor D3 (as shown in FIG. 2), which directs the flow of the second portion into channel 16 within the first reactor. The first reactant, first portion of the second reactant, and second portion of the second reactant generally combine in region 13 to produce the fourth mixture (for the exothermic reaction) in proximity to the downstream end of first reactor 7, which in this embodiment defines the upstream end of an exothermic reaction region 2063. For the description of the oxidation step, upstream and downstream are defined with respect to the average flow of the fourth mixture, and components and products thereof. Oxidant conducted through channels 15 and 16 and passages in the second reactor during the first interval reacts with the combustible non-volatiles deposited therein during preceding pyrolysis steps, thereby lessening the amount of accumulated combustible non-volatiles. A fifth mixture is directed by plenum 206A to at least one conduit (2066), and conducted away from the regenerative, reverse-flow pyrolysis reactor, the fifth mixture comprising at least a portion of the compositions resulting from the reaction of the fourth mixture's fuel and oxidant, compositions resulting from the oxidation of combustible non-volatiles in stage 206, and optionally at least a portion of any fourth mixture that is not to consumed in the reaction.

During the second interval of the oxidation step, valves V2, V4, V5, and V6 are closed. Valves V7, V8, V1, and V3 are open. The first reactant is conducted through at least one conduit 305 to optional second distributor D2, wherein D2 now directs the flow of the first reactant into channel 15 within first reactor 7. A first portion of the second reactant is conducted through at least one conduit 3051 to first distributor D1, wherein D1 now directs the flow of the first portion to channel 14 within first reactor 7. A second portion of the second reactant is conducted to the first reactor from conduit 3051, optionally through third distributor D3 (or plenum 206B as shown in FIG. 3) which directs the flow of the second portion into channel 16 within the first reactor. As in the first interval, the first reactant, first portion of the second reactant, and second portion of the second reactant generally combine in region 13 to produce the fourth mixture in proximity to the downstream end of first reactor 7. The fifth mixture is conducted away in the same as in the first interval. Oxidant conducted through channels 14 and 16 (and through passages of the second reactor) during the second interval reacts with the combustible non-volatiles deposited therein during preceding pyrolysis steps, thereby lessening the amount of accumulated combustible non-volatiles.

In an embodiment, ≥50.0 wt. %, e.g., ≥75.0 wt. %, such as ≥95.0 wt. % of the combustible non-volatiles in passages of the first and second reactors (e.g., channels 14, 15, and 16) are removed during the oxidation step, the weight percents being based on the weight of the accumulated combustible non-volatiles in the channels at the start of the second interval.

During all intervals of the oxidation step, it can be desirable to have comparable pressure drop (ΔP) across the length of the passages included in the first reactor (from fuel/oxidant inlet to mixer outlet, e.g., from face 9 to face 11 in FIG. 3). Comparable ΔP provides pressures in each passage that are similar to the pressures in neighboring passages, and thus limits the driving force for fuel and oxidant mixing prior to reaching the mixer end 11. Limiting fuel/air mixing upstream of region 13 leads to an increase in the amount of oxidation occurring in mixer region 13, which increases the selectivity and energy efficiency of the reactor system. Accordingly, in one embodiment, the relative number of passages constituting channels 14, 15, and 16 during a particular interval of the oxidation step is set to achieve approximately equal ΔP across the length of each passage in the first reactor. For example, during the first interval, the first reactant is carried by the first multi-purpose channel 14 and the second reactant is carried by the combination of second multi-purpose channel 15 and the second-reactant channel 16. The ratio of (i) the number of passages constituting the first multi-purpose channel to (ii) the number of passages constituting the second multipurpose channel and the second-reactant channel is selected so that that ΔP is substantially the same for all channels.

Conventional methods can be used for determining ΔP and for designing a reactor having channels of substantially equal ΔP, using, e.g., parameters such as passage dimensions, gas viscosity, gas velocity, etc. Conventional methods can be utilized for determining the proportion of passages needed to carry the fuel and oxidant in order to achieve similar ΔP, using, e.g., the relative flow rates of fuel and oxidant. The relative number of passages in each channel in each interval is most easily understood when the passages are all of equal dimension (as in honeycomb monoliths). However, the invention is not limited to such geometries, and may be applied to other structured or random packing creating constant or variable passage dimensions.

In many practical embodiments, the proportion of passages of the first reactor utilized for carrying fuel is much less than the proportion for carrying oxidant. For example, in a stoichiometric reaction of methane fuel with air oxidant, approximately 10 moles of methane react with approximately 100 moles of air. In an embodiment where (i) all passages have similar dimensions and (ii) the fuel and air have substantially similar gas properties (e.g., viscosity), approximately 10/110 (or about 9%) of the first reactor's passages are used to carry fuel at comparable $\Delta P$ with those carrying air. In other embodiments, the fuel passage:air passage number ratio (by number) is <0.09. For example, in embodiments where the fuel comprises ≥90.0 wt. % methane based on the weight of the fuel, the fuel passages can transport more moles of fuel at comparable $\Delta P$ to the air passages because methane has a lower viscosity than air. Other embodiments, e.g., those where the flow rate of oxidant-carrying stream is increased by addition of diluent or by the choice to operate with excess oxidant, utilize a further increase in the proportion of passages carrying oxidant during the oxidation step. Other embodiments, e.g., those where the flow rate of fuel-carrying stream is increased by addition of diluents or by the choice to operate with excess fuel, utilize an increase in the proportion of passages carrying fuel during the oxidation step. In an embodiment, the oxidation step is conducted for a time duration ($t_2$) sufficient for the second reactor to abstract sufficient heat from the oxidation to accomplish the pyrolysis step. The value of $t_2$ depends on factors, such as the geometry of the reactors utilized in stage 206, the heat transfer characteristics of the reactors and the materials from which the reactors are made, and the amount of heat needed by the pyrolysis step. Generally, the oxidation step is conducted for a time duration greater than or equal to a time sufficient for heating the pyrolysis region 2063 for exposing ≥50.0 wt. % of the first mixture, e.g., ≥75.0 wt. %, such as ≥90.0 wt. % to a temperature sufficient for thermally pyrolysing the first mixture to produce the desired second mixture; the weight percents being based on the weight of the first mixture. In an embodiment, $t_2$ is ≤10.0 seconds, e.g., ≤5.0 seconds, such as ≤1.0 seconds. Optionally, $t_2$ is in the range of 0.1 seconds to 100.0 seconds, e.g., in the range of 1.0 to 30.0 seconds.

Generally, the time duration of the oxidation step's first interval is selected for a time sufficient to remove ≥50.0 wt. %, e.g., ≥75.0 wt. %, such as ≥90.0 wt. %, of the combustible non-volatiles accumulated in channel 15 over a sequence of preceding pyrolysis steps. The weight percents are based on the total weight of combustible non-volatiles accumulated in channel 15 over a sequence of preceding pyrolysis step(s). Likewise, the time duration of second interval is selected for a time sufficient to remove ≥50.0 wt. %, e.g., ≥75.0 wt. %, such as ≥90.0 wt. %, of the combustible non-volatiles accumulated in channel 14 over a sequence preceding pyrolysis step(s). The weight percents are based on the total weight of combustible non-volatiles accumulated in channel 14 over a sequence of preceding pyrolysis step(s). The oxidation step can comprise the first and second interval only, but the invention is not limited thereto. In an embodiment, the first interval and second interval are repeated in sequence, one after the other, with no intervening pyrolysis step, until the desired time duration for the oxidation step is achieved. Such an embodiment can be beneficial when the second mixture contains a significant amount of combustible non-volatiles, which are deposited in the first reactor's channels. In an embodiment having a first reactor comprising two multi-purpose channels, the time duration of the first interval $t_{2a}$ is substantially equal to the time duration of the second interval $t_{2b}$. The term "substantially equal" in this context means $t_{2b}$ is within +/−20%, e.g. within +/−10% of $t_{2a}$. In the case where the oxidation step comprises a plurality of first intervals and at least one second interval, $\Sigma t_{2a}$: $\Sigma t_{2b}$ can be substantially equal; where $\Sigma t_{2a}$ represents the sum of the time durations of all first intervals in a single oxidation step and $\Sigma t_{2b}$ represents the sum of the time durations of all second intervals in a single oxidation step. The time duration of a single oxidation step $t_2$ is generally ≥$\Sigma t_{2a}$+$\Sigma t_{2b}$. For example, when there is substantially no dead time in switching valves v1-v4 from the first interval to the second, and when no purge fluid (e.g., a sweep gas) is utilized between the first and second intervals, $t_2$ is substantially equal to $\Sigma t_{2a}$+$\Sigma t_{2b}$. When $\Sigma t_{2a}$+$\Sigma t_{2b}$ is less than the amount of time needed for the second reactor to abstract sufficient heat from the oxidation to accomplish the pyrolysis step, oxidation of the fourth mixture can continue (e.g., as additional first and/or second intervals) until the reactor abstracts a sufficient amount of heat. In other words, the oxidation step can continue beyond the time duration needed to lessen the amount of deposits of combustible, non-volatile deposits in the pyrolysis reactor, e.g., when additional time is needed to heat the reactor for the pyrolysis step. For other embodiments, e.g., having a first reactor comprising >2 multi-purpose channels, time intervals can be determined utilizing the following guidelines: (i) the amount of reactant that flows through each multipurpose channel over all the intervals in the oxidation step should be substantially equal and (ii) the total time (over all the intervals in the oxidation step) that second reactant flows in each multipurpose channel should be sufficient to remove 90.0 wt. % of the combustible non-volatiles present in the multipurpose channel at the start of the oxidation step. In other embodiments, e.g., those having a first reactor having one multi-purpose channel (e.g., the embodiment of FIG. 5), the duration of $t_{2b}$ is generally within +/−20%, e.g. within +/−10% of the time needed to remove ≥90.0 wt. % of the combustible non-volatiles present in the multi-purpose channel at the start of the second interval.

After at least a portion of the fifth mixture is conducted away from region 2063, the first mixture is again conducted to region 2064, and the process repeats in sequence—exothermically reacting the fuel and oxidant of the fourth mixture to heat the reactor and then utilizing at least a portion of the heat for pyrolysing the first mixture. The first and second intervals of the oxidation step can be operated in sequence, one after the other, or alternatively, the first interval of the oxidation step can be followed by the pyrolysis step, the pyrolysis step then being followed by the second interval of the oxidation step.

The process can be operated sequentially, e.g., continuously, semi-continuously, or even in batch mode. In an embodiment, stage 206 comprises a plurality of pyrolysis reactors operating, e.g., in series, parallel, or a combination thereof, with at least one pyrolysis reactor having (i) pyrolysis step(s) and (ii) oxidation step(s) having the described first and second intervals. When stage 206 comprises a plurality of pyrolysis reactors, the sequence of oxidation steps and pyrolysis steps in each reactor can be out of phase, e.g., to provide a continuous flow of second mixture from the process. For example, in one embodiment stage 206 can comprise two reactor systems R1 and R2 operating in parallel. In this embodiment, the second mixture can be obtained from R1 undergoing a pyrolysis step while R2 is undergoing an oxidation step in a first period, and then in a second period, the second mixture is obtained from R2 undergoing a pyrolysis step while R1 is undergoing an oxidation step.

Although the process is described in terms of an embodiment utilizing valve means, e.g., mechanical valves such as poppet valves, ball valves, gate valves, etc., for directing the flow of the first reactant (via conduit 305) and the second reactant (via conduit 3051) into the appropriate channels of the first reactor 7 during the first and second intervals of the oxidation step, the invention is not limited thereto, and this description is not meant to foreclose other embodiments within the broader scope of the invention. For example, in another embodiment, reactor system 206 includes one or more movable (e.g., rotating or translating) vanes or spargers situated upstream of a stationary (with respect to the rotation of the vanes or spargers) first reactor 7. During the oxidation step, such vanes and/or spargers direct a continuous flow of first and second reactant into the passages of the reactor interfacing with the moving vanes or spargers. The sparger motion results in a changing proximity between sparger and passages. For example, a sparger associated with conduit 305 directs first reactant into the passages proximate to the sparger. As the sparger moves away from a passage, that passage is no longer proximate to the sparger, and may receive flow of second reactant via plenum 206B. In this embodiment, the multipurpose channel is comprised of all the reactor passages that are proximate to a moving sparger at any time during an oxidation step. Second-reactant passages are those passages that are not proximate to a moving sparger at any time during an oxidation step.

In yet another embodiment, typically stationary vanes and/or spargers can be used in combination with a moving (e.g., rotating) reactor 7 (e.g., a Ljungström geometry having (i) a rotating reactor or (ii) a fixed reactor with moving vanes). For example, reactor 7 can be in the form of an elongated cylinder having, e.g., a circular cross-section, with a rotational axis parallel to the reactor's axis of cylindrical symmetry. During the oxidation step, the motion of the sparger relative to that of the reactor has the same effect as the motion of the reactor relative to that of the sparger; that is, it creates a constantly changing proximity between sparger and passages resulting in a set of multipurpose passages. Optionally, the rotating reactor system 206 further comprises additional flow control means, e.g., additional vanes, which can be for (i) directing the flow of the first and/or second mixture into channels of first reactor 7 and (ii) for directing at least a portion of the second mixture toward conduit 2065, the average flow of the first and second mixtures being countercurrent to the direction of the fourth mixture's average flow. Optionally, the first 7 and second 1 reactors have a common axis of cylindrical symmetry with the second reactor rotating about such axis in synchronization with the rotation of the first reactor and/or the flow-control means. One benefit of the rotating reactor is that the rotating reactor(s) and/or vanes can be operated to permit the simultaneous operation of (i) the pyrolysis step and (ii) the first and second intervals of the oxidation step continuously within stage 206, with the average flow of the first and second mixtures being countercurrent to the average flow of the fourth and fifth mixtures. Motor means can be used to drive the rotational motions utilized in these embodiments. Such motor means can be (a) external to stage 206, e.g., as in the case of an electric motor and associated transmission of rotational energy, or (b) derived in part from hydrodynamic forces in stage 206. When the first reactor is a moving (e.g., rotating) reactor utilized in combination with fixed and/or movable flow control means utilized to direct the flow of the first and second reactants into the first reactor's channels, the relationship between the reactor's passages and channels changes from interval-to-interval of the oxidation step. In other words, the sequencing of first and second reactant during the intervals of the oxidation step depends on the relative motion of (i) the flow control means and (ii) the reactor's passages. In such embodiments, the moving reactor comprises at least one multi-purpose channel, the multi-purpose channel comprising a passage or set of passages fed by the first reactant during at least one first interval of the oxidation step and which are fed by the second reactant during at least one second interval of the oxidation step, the second interval occurring before or after the first interval. The reactor can, e.g., further comprise a second-reactant channel, comprising a set of passages that do not convey the first reactant during any interval of the oxidation step.

When valve means are utilized to direct the flow of the first, second, fourth, and fifth mixtures, at least some of the valve means can be hydrodynamic valve means. For example, in an embodiment illustrated in FIG. 4 and FIG. 5, the function of valves V1 and V2 are executed by the hydrodynamics of the reactor and distributor design, and a single valve V8 controls the flow of all of the second reactant (first and second portions). In such embodiments, distributor D1 is configured for (i) directing the flow of the first reactant to channel 14 when flow of the first reactant emerges from D1 (during the first interval) and (ii) directing the flow of the first portion of the second reactant around D1 via flow-path 20 toward channel 14 when the flow of first reactant does not emerge from D1 (during the second interval), as a result of hydrodynamic forces present in the reactor and D1. The second portion of the second reactant flows from distributor D3 (or alternatively via plenum 206B) toward channel 16 during the first and second intervals. It can be advantageous to utilize hydrodynamic valving when the first reactor 7 comprises sections as described in more detail below in connection with the high temperature thermal pyrolysis of hydrocarbon. The use of hydrodynamic valving, reactor sections, etc., is not limited to embodiments utilizing a high-temperature thermal pyrolysis of hydrocarbon.

Optionally, the process further includes one or more of the following components: treating/upgrading stage 308 for treating and/or upgrading the fifth mixture downstream of conduit 2066; one or more conduits for adding to the fourth mixture's fuel source material 300; one or more of molecular hydrogen and/or light saturated hydrocarbon, such as methane 3001 or diluent, such as oxygenate 3002; conduits for adding to the fourth mixture's oxidant source material 301 additional or supplemental oxidant 3003 or diluent 3004; one or more conduits for adding to the first source material one or more of molecular hydrogen 2043, hydrocarbon, e.g., light saturated hydrocarbon such as methane 2044, or diluent, such as oxygenate 2045; one or more conduits for conducting away heteroatom species, such as hydrogen sulfide or non-volatiles 2041; one or more conduits for conducting away a first byproduct from upgrading stage 308, the first byproduct including at least one of non-oxidized hydrocarbon 3081 and/or, diluent such as oxygenate 3082; a conduit 3083 for conducting heteroatom species such as $NO_x$, $SO_x$, $CO_2$, $N_2$, sulfuric acid, etc., away from upgrading stage 308; one or more conduits for conducting a second byproduct away from stage 208, the second byproduct including, e.g., one or more of molecular hydrogen 2082 or light saturated hydrocarbon 2083; one or more conduits for conducting away non-volatiles 2084 and/or heteroatom species, such as hydrogen sulfide 2085 away from upgrading stage 208; or one or more conduits (not shown) for adding to the second mixture one or more of (i)

hydrogen; (ii) methane, ethane, and/or other light saturated hydrocarbon; or (iii) ethylene.

One embodiment of the process will now be described in more detail with reference to the reactor system shown schematically in FIG. 4. In this embodiment, the first interval of the oxidation step, the second interval of the oxidation step, and the pyrolysis step are operated continuously in sequence. This description is not meant to foreclose other embodiments within the broader scope of the invention, such as those which, e.g., (i) utilize more than one pyrolysis reactor, (ii) have a pyrolysis step between the first and second intervals of the oxidation step, have additional oxidation intervals whether in sequence or otherwise, or (iii) are not operated continuously.

VI. Continuous Process Utilizing Hydrodynamic Valving

In one embodiment, the invention relates to a continuous process for converting a first mixture comprising hydrocarbon to a second mixture comprising ≥1.0 wt. % $C_2$ unsaturates and ≥1.0 wt. % combustible, non-volatiles (based on the weight of the second mixture) by exposing the first mixture to a temperature ≥1.20×10$^{3o}$ C. under thermal pyrolysis conditions in a pyrolysis region of a regenerative, reverse-flow thermal pyrolysis reactor. At least a portion of the heat utilized by the pyrolysis is provided by providing a fourth mixture comprising first and second reactants to an oxidation region of the regenerative, reverse-flow thermal pyrolysis reactor, and oxidizing the first reactant's fuel component. The relative amounts of the first and second reactants; the types and amounts of fuel in the first reactant; the types, locations, and amounts of combustible non-volatiles present in stage 206 during the oxidation step; and the types and amount of oxidant in the second reactant are selected so that the (exothermic) heat of reaction obtained during the oxidation step sufficiently heats the pyrolysis region, particularly the portion of the pyrolysis region that is coextensive with the oxidation region, for exposing the first mixture to a temperature ≥1.20×10$^{3o}$ C., e.g., ≥1.40×10$^{3o}$ C., and lessens the accumulation of combustible non-volatiles. In this embodiment, the oxidation step comprises first and second intervals, the first and second intervals having no intervening pyrolysis step.

Figure 4:
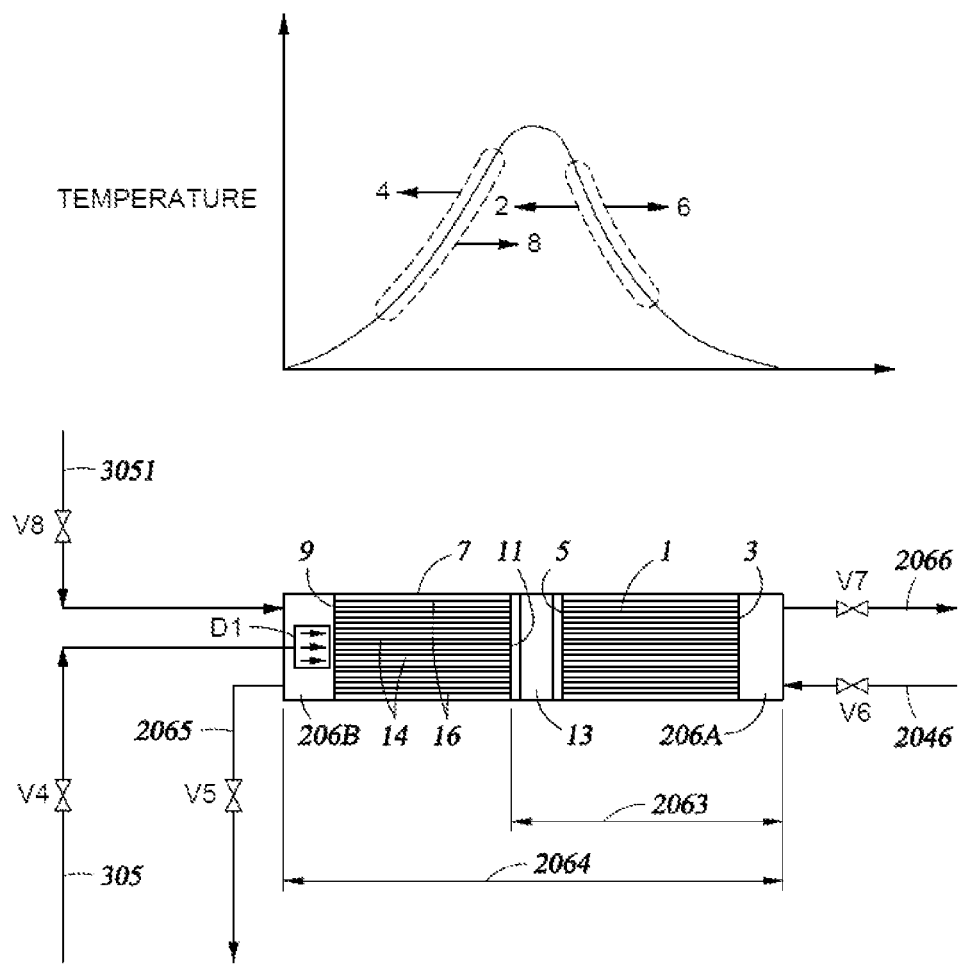
FIG. 4 schematically shows yet another a reverse-flow pyrolysis reactor useful in the system of FIG. 1.

In this embodiment, pyrolysis stage 206 utilizes hydrodynamic valving and at least one regenerative-reverse-flow thermal pyrolysis reactor system as illustrated schematically in FIG. 4. Stage 206 comprises two reactors: a first (recuperator/quenching) reactor 7 and a second (pyrolysis/reforming) reactor 1, the first reactor 7 comprising (i) a multi-purpose channel 14 and (ii) a second-reactant channel 16, which is utilized for conducting a portion of the second reactant during the first and second intervals.

Figure 4A:
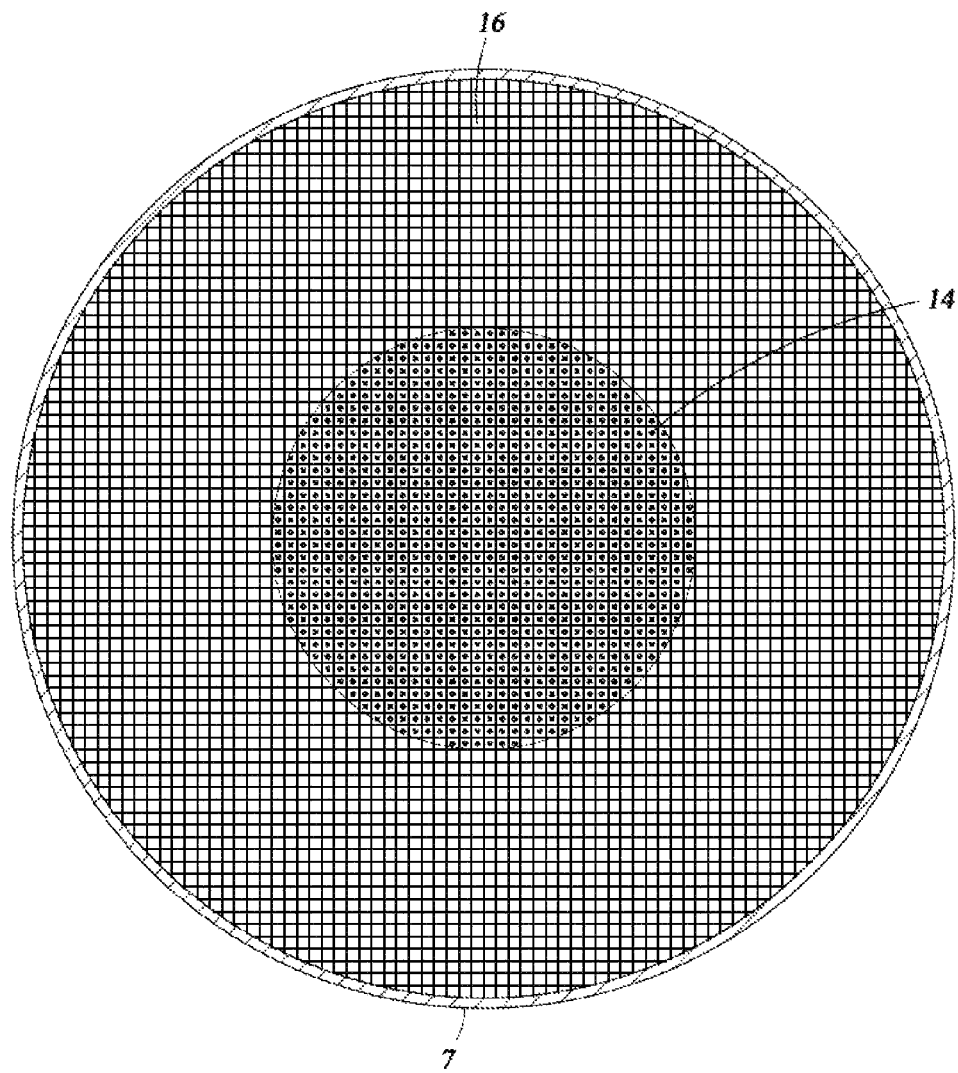
FIG. 4A schematically shows a top view of the reactor of FIG. 4.

The first and second reactors comprise regenerative beds, the regenerative beds comprising bedding or packing material, such as one or more of glass or ceramic beads or spheres; metal beads or spheres; (i) ceramic, including, e.g., alumina, silica, yttria, zirconia, etc., and mixtures thereof; or (ii) metal honeycomb materials; ceramic tubes; extruded monoliths catalysts; etc. The materials comprising the regenerative bed are selected to maintain integrity, functionality, and withstand long term exposure to temperatures ≥700° C., e.g., ≥1200° C., such as ≥1500° C., or even ≥2000° C. for operating margin. The first and second reactors can be, e.g., the same as those described in U.S. Pat. No. 7,943,808. The shape of the regenerative beds is not restricted to any particular geometry. For example, the first and second reactors can be elongated, and can have elliptical, cylindrical, and/or rectangular cross-sections, including combinations thereof. The reactors can be of the same shape and size, but this is not required. For example, the first reactor can be in the form of a honeycomb monolith of substantially cylindrical cross-sections. The first reactor's channels each comprise a plurality of passages, the passages comprising substantially parallel, substantially independent flow-paths within the regenerative media, e.g. within the honeycomb. The passages can each be of the same size, shape, and ΔP, for example. Channel 14 comprises the set of passages whose entrance interfaces with (e.g., are proximate to) distributor D1, as identified by the reference number 14 in FIG. 5. Channel 16 comprises the set of passages whose entrance interfaces with (e.g., are proximate to) distributor D3 identified by the reference number 16 on FIG. 5. The scale of FIG. 4 does not permit perfect representation of the relationship between passages and distributors. However, channel 14 generally comprises the passages proximate to the distributor D1, while channel 16 generally comprises all other channels that are accessible to plenum 206B, as shown in FIG. 4A for a sparger having a cylindrical geometry.

In an embodiment, ≥50.0 wt. %, e.g., ≥75.0 wt. %, such as ≥90.0 wt. % of the second reactant is conducted to region 206 3 by channel 16 during the first interval of the oxidation step and by the channels 14 and 16 during the second interval, the weight percent being based on the total weight of the second reactant. Optionally, the first reactor 7 further comprises means for supplying additional fuel to region 206 3, e.g., by a first-reactant conduit (not shown) external to first reactor 7 and/or a first-reactant channel (not shown) located within first reactor 7. Optionally, such means are utilized solely for conducting the additional fuel (as, e.g., first reactant) toward region 206 3. The invention is compatible with this use of such first-reactant channels, and optionally for conducting the first and/or second mixture away from region 206 4 during the pyrolysis step, though it can be undesirable to do so. For example, combustible non-volatiles can accumulate in such first-reactant channels as a result of deposits formed as a result of (i) the pyrolysis steps or (ii) the oxidation step for fuels a tendency to form deposits such as coke. The accumulation of such deposits in the first-reactant channel is not diminished during the oxidation step because the second reactant is generally excluded from the first-reactant channels. In an embodiment, ≥50.0 wt. %, e.g., ≥75.0 wt. %, such as ≥90.0 wt. % of the first reactant is conducted to region 206 3 by channel 14 during the first interval of the oxidation step, the weight percents being based on the total weight of the first reactant.

Optionally, one or more mixer means are used between the first and second reactors to improve the oxidation reaction. Mixer means, distributor means, reactor system internals, flow-control means, etc., for the reactor system included in stage 206 can be substantially the same as those described in U.S. Pat. No. 7,943,808, for example.

It is understood that flow control means (e.g., one or more of valves, rotating reactor beds, check valves, louvers, flow restrictors, timing systems, etc.) can be used to control gas flow, actuation, timing, and to alternate physical beds between the flow systems for the first, second, fourth, and fifth mixtures, and the optional purge gas when used. For example, stage 206 can further comprise means for conveying fuel (via conduit 305) and to oxidant (via conduit 3051) into the appropriate channels in the first reactor. Such means can include, e.g., one or more of plenums, valves, vanes, spargers and/or distributors. Suitable spargers, distributors, etc., are disclosed in U.S. Pat. No. 7,815,873; which is incorporated by reference herein in its entirety. Although the invention is compatible with the use of conventional spargers, distributors, plenums, etc, in stage 206, the invention is not limited thereto.

The oxidation step will now be described in more detail.

Oxidation Step

The oxidation step begins by conducting first and second reactants to the first reactor 7. The first reactant is conducted to first reactor 7 via conduit 305. The second reactant is conducted to the first reactor by conduit 3051, optionally substantially simultaneously with the conduction of the fuel in conduit 305. In the embodiment illustrated in FIG. 4, the first and second reactants do not mix appreciably upstream of end 11 of first reactor 7, e.g., ≥80.0% of the mixing of the first and second reactants by weight, such as ≥90.0%, occurs downstream of end 11 of first reactor 7. The invention is not limited to this embodiment, and this description is not meant to foreclose other embodiments within the broader scope of the invention, such as embodiments where there is a significant amount of fuel and oxidant mixing in the first reactor. Continuing with the embodiment illustrated in FIG. 4, proximate to the downstream end 11 of the first reactor 7, the first and second reactants combine to produce a fourth mixture. The fuel and oxidant of the fourth mixture react exothermically at or proximate to a central region 13 of the reactor system. Optionally, the exothermic reaction continues downstream (with respect to the average flow of the fourth mixture) of region 13, e.g., in second reactor 1. The fifth mixture is conducted away from second reactor 1 via one or more conduits 2066. The oxidation step can result in a high temperature zone (also referred to by those skilled in the art as a temperature bubble), at least a portion of the temperature bubble being located in region 2063. The temperature bubble is illustrated schematically as a Gaussian-like shape in FIG. 4.

The oxidation step thus includes the following features: (i) heating of region 13 and the second reactor 1 by transferring at least a portion of the heat of combustion to the reactor system downstream of the end 11 of the first reactor 7 and (ii) by transferring at least a portion of the sensible heat recovered by the first and second reactants in an upstream region of the first reactor (upstream with respect to the flow of the first and second reactants) toward one or more of the downstream region of the first reactor, region 13, or the second reactor in order to thermally regenerate the reactor system. Accordingly, at least a segment of each of the right-hand and left-hand edges the temperature profile translate downstream from their starting locations at the beginning of the oxidation step, as shown in FIG. 4 by arrows 6 and 8. It should be recognized that the translations indicated by arrows 2, 4, 6, and 8 of the temperature profile's edges during the oxidation and pyrolysis steps confines the temperature profile (which can achieve temperatures e.g., >1600° C.) to regions of the reactor system that can tolerate such conditions long-term. Optionally, the shift in the edges of the temperature profile is accompanied by a shift in the position of the peak of the temperature profile. Operating conditions during the oxidation step can be substantially the same as those disclosed in U.S. Pat. No. 7,943,808. In an embodiment, the exothermic reaction of the fuel and oxidant components of the fourth mixture includes combustion, the combustion conditions including a temperature ≥1.40×10³° C., e.g., ≥1.50×10³° C., such as ≥1.60×10³° C., e.g., in the range of 1.90×10³° C. to 2.20×10³° C., and a pressure ≥1.0 bar (absolute), e.g., in the range of 1.0 bar to 15.0 bar, such as 2.0 bar to 5.0 bar.

Optionally, the oxidation step oxidizes ≥90.0 wt. % of the first reactant's fuel component e.g., ≥99.0 wt., % based on the weight of the first reactant's fuel component. Optionally, diluent, such as nitrogen, that may be present in the fourth mixture is not oxidized to a significant extent. Optionally, ≥50.0% of the oxidation of the fourth mixture (based on amount of the fourth mixture, mole basis, that is oxidized in region 2063), e.g., ≥75.0%, such as ≥90.0% of the oxidation occurs in the portion of region 2063 that is located between the first and second reactors.

In this embodiment, the total duration of an oxidation step $t_2$ is for a time sufficient for the second reactor to abstract sufficient heat from the oxidation to accomplish the pyrolysis step. In other words, the oxidation step is conducted for a time duration greater than or equal to a time sufficient to displace the peak of the temperature toward the second reactor sufficient to heat the pyrolysis region 2064 for exposing the first mixture to a temperature ≥1.20×10³° C. during the pyrolysis step. Optionally, $t_2$ is in the range of 0.1 seconds to 30.0 seconds. Optionally, the total amount of heat added to the reactor system during the oxidation step (also called the "regeneration" step) does not exceed the sum of the heats that are required (a) to sustain the pyrolysis reaction for endothermically driving the second mixture from the pyrolysis portion of the first mixture and (b) for heat losses from the system, e.g., by as conduction losses through reactor walls and/or convective losses with, e.g., the second mixture. Optionally, the total amount of heat stored in the reactor system is generally much more than the minimum amount of heat needed for the pyrolysis step.

In order to lessen the accumulation of deposits, such as combustible non-volatiles (e.g., coke) in stage 206, particularly those present in the passages of first reactor 7, the oxidation step is divided into first and second intervals, which will now be described in more detail.

Oxidation Step—First Interval

Figure 5:
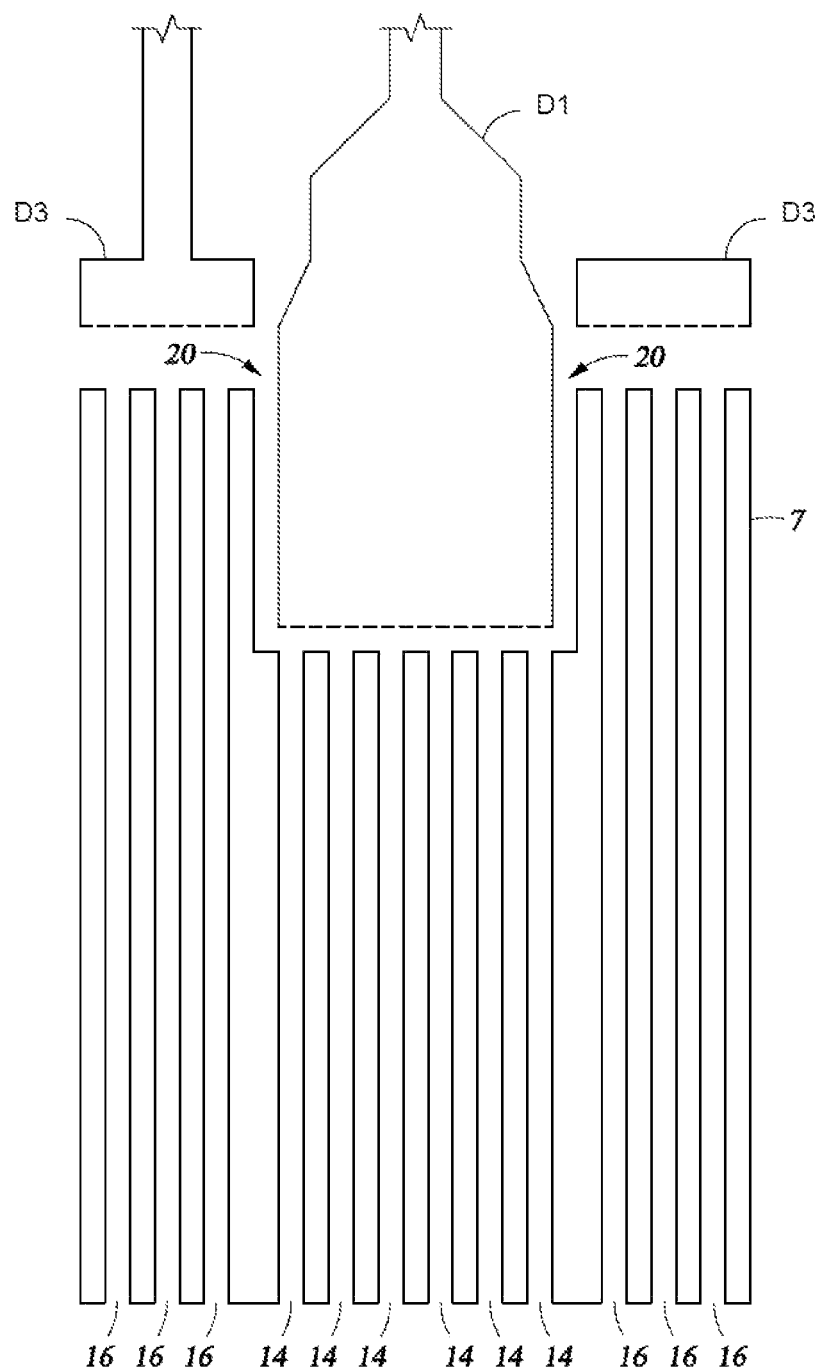
FIG. 5 schematically shows a section view of reactant distributors and a reactor bed that can be utilized in the reactor of FIG. 4.

Referring to FIG. 4, valves V8, V7, and V4 are open during the first interval of the oxidation step and valves V5 and V6 are closed. The first reactant is conducted through conduit 305 to first distributor D1, which directs the flow of the first reactant into channel 14 within first reactor 7. An end-view of reactor 7, illustrating the approximate location of distributor D1 (the shaded area), is provided in FIG. 4A. Optionally, the downstream end of D1 is located within a counter bore of first reactor 7, as shown in FIG. 5. At least a portion of the second reactant is conducted through conduit 3051 to second plenum 206B, which directs the flow of the oxidant to channel 16 within first reactor 7. A portion of the second reactant in channel 16 is consumed oxidizing combustible non-volatiles located therein. The first reactant and unreacted second reactant combine in region 13 to produce the fourth mixture (for the exothermic reaction) in proximity to the downstream end of first reactor 7, upstream and downstream being defined for the oxidation intervals with respect to the average flow of the fourth mixture and components thereof. The fifth mixture is directed by plenum 206A to conduit 2066, and conducted away from the regenerative, reverse-flow pyrolysis reactor. At least a portion of the heat of combustion of combustible non-volatiles in stage 206 and the first reactant's fuel component is utilized to increase the temperature of region 2064. In embodiments where the second reactant reacts with a significant amount of combustible non-volatiles in the passages of first reactor 7, the upstream end of region 2063 may be located to the left (upstream) of the position shown in FIG. 4.

Optionally, the size and locations of distributor D1 are selected to lessen the amount of mixing of first and second reactant upstream of region 13. Optionally, the size and locations of D1 are selected to substantially equalize (within, e.g., +/−25%, such as +/−10.0%) the gas velocities of the first reactant through the passages of channel 14 and the second reactant through the passages of channel 16. Optionally, the number and cross-sectional areas of passages comprising channels 14 and 16 are selected to approximately equalize (within, e.g., +/−25%, such as +/−10.0%) the ΔP among the channels.

Oxidation Step—Second Interval

During the second interval of the oxidation step, valves V4, V5, and V6 are closed. Valves V8 and V7 are open. Since the first reactant is blocked from distributor D1 by valve V4, the first reactant does not flow into (or emerge from) D1 during this interval. A to first portion of the second reactant flows from conduit 3051 via gap 20 between distributor D1 to channel 14. Although gap 20 as shown in FIG. 5 is located within a counter bore of first reactor 7, the invention is not limited to this configuration. For example, when face 9 of first reactor 7 is substantially flat (e.g., has little or no counter bore opposite the adjacent face of D1), gap 20 is the space located between face 9 and the adjacent face of D1. The first portion of the second reactant oxidizes combustible non-volatiles located in channel 14. A second portion of the second reactant flows from plenum 206B into channel 16. The second portion of the second reactant oxidizes any combustible non-volatiles as might remain in the channel after the first interval. As is the case in the first interval, the fifth mixture can be conducted away from stage 206.

Optionally, (i) the first portion of the second reactant comprises 30.0 wt. % to 70.0 wt. % of the second reactant and (ii) the second portion of the second reactant comprises 30.0 wt. % to 70.0 wt. % of the second reactant, the weight percents being based on the total weight of the second reactant provided to stage 206 in the second interval. Optionally, the weight ratio of first amount:second amount is in the range of 0.5 to 2.0, e.g., about 0.8 to 1.2. Optionally, the size and location of distributor D1 and plenum 206B are substantially the same as in the first interval.

Generally, the time duration of first interval $t_{2a}+t_{2b}$ is selected to accomplish regeneration of first reactor 7. Time intervals $t_{2a}$ and $t_{2b}$ can be independently selected. For example, in an embodiment, the time duration of second interval $t_{2b}$ is greater than or equal to the amount of time needed for removing ≥50.0 wt. %, e.g., ≥75.0 wt. %, such as ≥90.0 wt. % of the combustible non-volatiles accumulated in channel 14 over a sequence of preceding pyrolysis step(s). The weight percents are based on the total weight of combustible non-volatiles accumulated in channel 14 over a sequence of preceding pyrolysis step(s) (and first interval(s) when the first reactant can deposit combustible non-volatiles). Should combustible non-volatiles deposit in D1, e.g., during the first interval, these can be removed by conducting oxidant through D1 during the second interval. The oxidation step can comprise the first and second intervals only, but the invention is not limited thereto. For example, in an embodiment, the first interval and second interval are repeated in sequence, one after the other, with no intervening pyrolysis step, until the desired time duration for the oxidation step is achieved. Optionally, $t_{2a}$ and $t_{2b}$ are each in the range of 0.1 seconds to 15.0 seconds.

The invention is not limited to embodiments where the channels in the first reactor 7 comprise two contiguous regions only. For example, in other embodiments, first reactor 7 comprises a honeycomb monolith in the form of an elongated polygonal body. The honeycomb comprises at least two sections, the sections being in side-to-side contact, with each section having, e.g., (i) at least one multi-purpose channel and (ii) at least a portion of those passages of reactor 7 constituting second-reactant channel(s). In one embodiment, first reactor 7 is a honeycomb in the form of an elongated rectangular body having upstream and downstream faces of substantially equal rectangular cross-sections. The honeycomb comprises four sections $S_1$-$S_4$ joined side-to-side, the sections each being honeycombs in the form of an elongated rectangular body having upstream and downstream faces of substantially equal rectangular cross-sections. In this embodiment, each section comprises two sets of passages, with one set of passages ("$S_{mp}$") constituting a multi-purpose channel and the second set of passages ("$S_{sr}$") constituting a portion of reactor 7's second-reactant channel. Sets $S_{mp1}$ and $S_{sr1}$ are located in $S_1$, sets $S_{mp2}$ and $S_{sr2}$ are located in $S_2$, sets $S_{mp3}$ and $S_{sr3}$ are located in $S_3$, and sets $S_{mp4}$ and $S_{sr4}$ are located in $S_4$. Sets $S_{mp1}$, $S_{mp2}$, $S_{mp3}$, and $S_{mp4}$ each constitute a multi-purpose channel: $C_1$, $C_2$, $C_3$, and $C_4$. Sets $S_{sr1}$, $S_{sr2}$, $S_{sr3}$, and $S_{sr4}$ constitute one second-reactant channel: $C_5$. Channels $C_1$-$C_4$ are of substantially equal cross-sectional area and have openings located within a circular region approximately centered on the faces of sections $S_1$-$S_4$ ($C_1$ centered on the face of $S_1$, $C_2$ centered on the face of $S_2$, etc.).

The oxidation step comprises four intervals, during which the flow of first and second-reactants is sequenced as follows:

(i) During the first interval, the first-reactant is conducted through $C_1$, $C_2$, and $C_3$. A first portion of the second-reactant is conducted through $C_4$.

(ii) During the second interval, the first-reactant is conducted through $C_1$, $C_2$, and $C_4$. A first portion of the second-reactant is conducted through $C_3$.

(iii) During the third interval, the first-reactant is conducted through $C_1$, $C_3$, and $C_4$. A first portion of the second-reactant is conducted through $C_2$.

(iv) During the fourth interval, the first-reactant is conducted through $C_2$, $C_3$, and $C_4$. A first portion of the second-reactant is conducted through $C_1$.

During each of the first-fourth intervals, the first portion of the second reactant is conducted through one of the multipurpose channels ($C_1$-$C_4$), the volumetric flow rate of this portion being roughly comparable (after adjusting for viscosity) to the volumetric flow rate of ⅓ of the first reactant, which is the amount of first reactant that flows in each of the other multipurpose channels ($C_1$-$C_4$), in order to maintain roughly comparable pressure drop among the passages. A second portion of the second reactant comprising roughly the remainder of the second-reactant is conducted through $C_5$, in an amount that depends, e.g., on the amount of diluent (if any) in the first and second reactants; typically ≥50.0 wt. %, e.g., ≥75.0 wt. %, such as ≥90.0 wt. % based on the weight of the second reactant. Optionally, the flow rates of first reactant, second reactant, and the first and second portions of the second reactant are substantially the same (+/−25.0%, e.g., +/−10.0%) during each interval. When flow rates are substantially constant over the intervals, the relative amount of a given stream that is conducted during a given interval (e.g., the amount of first reactant that is conducted during the first interval) will be in proportion to the duration of the interval. The use of a plurality of sections can be advantageous when it is desirable to combine and react at least a portion of each of the first and second reactants during all intervals of the oxidation step.

The use of multiple honeycomb sections (as in $S_1$-$S_4$) facilitates the application to large-diameter reactor systems. In some embodiments, each section utilizes one mixer in region 13 to facilitate mixing of the first and second reactants that are flowing predominantly through the passages in that section. In those embodiments, there may be roughly the same number of mixers as there are sections. In large-diameter reactors, the number of sections may be very large, numbering in the dozens or even hundreds. Since a set of passages in each section (the $S_{sr}$) conveys the second reactant, such embodiments do not require a separate oxidation step interval for each section. For example, in one embodiment, the reactor system comprises (i) a first reactor comprising 100 sections and four divisions (25 sections per division) and (ii) one mixer per section. In such an embodiment, the oxidation step can comprise four intervals, e.g., with multipurpose channel $C_1$ comprising the combination of all the multipurpose passages in the 25 sections of the first division, e.g., $S_{mp1}$ to $S_{mp25}$, and multipurpose channel $C_2$ comprising the combination of all the multipurpose passages in the 25 sections of the second division, e.g., $S_{mp26}$ to $S_{mp50}$, etc. Each of channels $C_1$-$C_4$ may be fed by a single distributor, e.g., with 25 spargers, e.g., one for each section. The combination of all the sets of second-reactant passages, $S_{sr1}$, to $S_{sr100}$ constitute one second-reactant channel ($C_5$). A combination of hydrodynamic and mechanical valving can be utilized to direct the flow of the first reactant and first portion of the second reactant to channels $C_1$ and $C_4$ as described above for the four-section embodiment. A second portion of the second reactant can flow to $C_5$ during all four intervals.

Mixing means suitable for combining the first and second reactants during the first—fourth intervals are described in U.S. Pat. No. 7,943,808. FIG. 4 of that patent illustrates mixing means suitable for use with a first reactor 7 comprising a honeycomb having 7 sections, though this embodiment is not limited to that configuration. FIG. 4A that patent illustrates mixing means suitable for use with single or multiple sections. Other suitable mixing means for single or multiple sections are shown in FIGS. 4, 5, and 6 of U.S. Pat. No. 7,815,873. For example, when a honeycomb of four sections is used, a mixer of the type illustrated in U.S. Pat. No. 7,943,808's FIG. 4A can be located in each section, each mixer being approximately centered with one of $C_1$, $C_2$, $C_3$, or $C_4$ on an axis parallel to the honeycomb's long axis.

The oxidation steps of the preceding embodiments can be utilized in any of the pyrolysis reactor systems of stage 206. Referring now to FIG. 1, when it is desired to (a) increase the relative amount of one or more of hydrocarbon (e.g., methane) and/or hydrogen in the fuel over that of its source material or (b) increase the relative amount of oxidant (e.g., oxygen and/or ozone) in the oxidant over that of its source material, this can be done as follows:
(a) Hydrocarbon, such as light saturated hydrocarbon, e.g., methane, can be added via conduit 3001. These species can be obtained from (i) external sources and/or (ii) sources within the process, such as from conduits 3081 or 2083, e.g., when optional stages 308 and 208 are utilized.
(b) Oxidant can be added via conduit 3003. The added oxidant can be obtained from (i) external sources and/or (ii) sources within the process such as from conduit 3082, e.g., when optional stage 308 is utilized and the oxygenate in conduit 3082 comprises oxidant. When the source material is air, the air can be obtained from a blower or compressor, for example.

Continuing with reference to FIG. 1, at the conclusion of the oxidation step optional upgrading stage 308 can be used, e.g., to separate from the fifth mixture species that may be useful in other stages of the process, e.g., via conduits 3081-3083 as discussed, e.g., diluent can be separated from the fifth mixture and utilized to produce the fourth mixture.

At the conclusion of the pyrolysis step, optional upgrading stage 208 can be used, e.g., to separate from the second mixture species that may be useful in other stages of the process, e.g., via conduits 2082. The portion of the second mixture that is not used in other stages of the process can be conducted away from the process via one or more conduits (2087) for storage or further processing. Conventional separations processes are useful for stage 208 and 308, though the invention is not limited thereto.

Pyrolysis Step

After the oxidation step, the pyrolysis portion of the first mixture is conducted via conduit 2046 to the upstream end of region 2064, e.g., the upstream end of the second reactor, where upstream is now defined with respect to the flow of the first and second mixtures. Referring to FIG. 4, plenum 206A distributes the first mixture into the channels of second reactor 1, which have been heated by the preceding oxidation step. Optionally, a reactor purge can be used between the oxidation and pyrolysis steps. During the pyrolysis step, valves V4, V7, and V8 are closed. Valves V5 and V6 are open. The vapor-phase portion of the second mixture is directed away from region 2064 by plenum 206B, the vapor-phase portion of the second mixture being conducted away via conduit 2065. A second portion of the second mixture, comprising combustible non-volatiles, remains in the reactor system as a deposit, e.g., in channels 14 and 16.

At the start of the pyrolysis step, (a) the downstream end 5 of the second reactor 1 (downstream with respect to the flow of the first mixture, as shown in FIG. 4) is at a temperature greater than that of the upstream end 3 and (b) at least a portion (including the downstream end 9) of the first reactor 7 is at a temperature less than that of the downstream end of the second reactor 5 in order to provide a quenching effect for the second mixture.

The first mixture is exposed to a temperature $\geq 1.20 \times 10^{3\circ}$ C., e.g., $\geq 1.50 \times 10^{3\circ}$ C., under high-severity thermal pyrolysis conditions. Generally, the first mixture is exposed to these conditions in the portion of region 2064 that is coextensive with region 2063 via proximity to the second reactor and other reactor internals (e.g., mixer media) located, e.g., in the temperature profile region, which have been heated, such as by the exothermic reaction of the fuel and oxidant during a preceding oxidation step. Optionally, at least a portion of the temperature bubble region is located within the portion of zone 2064 that is coextensive with zone 2063.

Continuing with reference to FIG. 4, the first mixture abstracts heat from the first reactor, resulting in the derivation of the second mixture from the first by pyrolysis. As this step proceeds, a shift in the temperature profile occurs, e.g., a shift in at least a segment of the right-hand edge of the temperature profile (the segment being schematically encompassed by a dashed boundary for the purpose of illustration), the direction of the shift being indicated by arrow 2. The amount of this shift can be influenced by, e.g., the heat transfer properties of the system. At least a portion of the second mixture, e.g., the portion in the vapor phase, is conducted from the downstream end 5 of the second reactor to the upstream end 11 of the first reactor 7, and is conducted away from the first reactor via conduit 2065 proximate to the downstream end 9, as shown. At the start of pyrolysis, the first reactor 7 has a temperature less than that of the second reactor 1. As the second mixture traverses the first reactor 7, the second mixture is quenched (e.g., cooled) to a temperature to approaching that of the downstream end 9 of the first reactor. As the second mixture is quenched in the first reactor 7, at least a segment of the left-hand edge of the temperature profile moves toward the downstream end 9 of the first reactor 7 as indicated by arrow 4, the segment being schematically encompassed by a dashed boundary for the purpose of illustration. In at least one of the embodiments represented by FIG. 4, the upstream end of pyrolysis region 2064 is proximate to the upstream end 3 of the second reactor 1. The downstream end of pyrolysis region 2064 is proximate to the downstream end 9 of the first reactor 7. Since the quenching heats the first reactor 7, the oxidation step optionally includes cooling the first reactor, e.g., to shift at least a segment of the left-hand edge of the temperature profile away from end 9 of the first reactor 7, as illustrated schematically by arrow 8 in FIG. 4.

In an embodiment, the pyrolysis step includes one or more of the following conditions: the first mixture achieves a peak pyrolysis gas temperature $\geq 1.40 \times 10^{3}$° C., e.g., in the range of $1.45 \times 10^{3}$° C. to $2.20 \times 10^{3}$° C., such as, $1.50 \times 10^{3}$° C. to $1.90 \times 10^{3}$° C., or $1.60 \times 10^{3}$° C. to $1.70 \times 10^{3}$° C.; a total pressure $\geq 1.0$ bar (absolute), e.g., in the range of 1.0 bar to about 15 bar, such as in the range of 2.0 bar to 10.0 bar; a high-severity residence time $\leq 0.1$ seconds, e.g., $\leq 5.0 \times 10^{-2}$ seconds, such as $\leq 5.0 \times 10^{-3}$ seconds and/or a $t_1$ in the range of $1.0 \times 10^{-3}$ seconds to 10.0 seconds. Optionally, the first mixture comprises $\geq 0.01$ mole % of hydrocarbon, e.g., 0.1 mole % to 90.0 mole % of hydrocarbon and $\geq 0.01$ mole % of molecular hydrogen, e.g., 0.1 mole % to 90.0 mole % of molecular hydrogen, the mole percents being based on the sum of the number of moles of hydrocarbon and hydrogen in one mole of the first mixture. When it is desired to increase the amount of one or more of molecular hydrogen, hydrocarbon (e.g., light saturated hydrocarbon such as methane), and diluent in the first mixture, these can be added (e.g., in stage 204) as follows:

(i) Molecular hydrogen can be added via conduit 2043, with the added hydrogen obtained, e.g., from one or more of (a) from the process via conduit 2082 when optional stage 208 is present, (b) from molecular hydrogen separated from the first product, or (c) from an external source.

(ii) Hydrocarbon can be added via conduit 2044. These species can be obtained from the process via conduit 3081 or 2083, e.g., when optional stages 308 and 208 are utilized, from hydrocarbon separated from the first product, or from an external source.

(iii) Diluent (such as oxygenate) can be added via conduit 2045. The diluent can be obtained, e.g., (a) from the process via conduit 3082, when optional stage 308 is utilized, (b) from the first product, (c) from the second mixture, and/or (d) from a source external to the process.

All patents, test procedures, and other documents cited herein, including priority documents, are fully incorporated by reference to the extent such disclosure is not inconsistent and for all jurisdictions in which such incorporation is permitted.

While the illustrative forms disclosed herein have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside herein, including all features which would be treated as equivalents thereof by those skilled in the art to which this disclosure pertains.

When numerical lower limits and numerical upper limits are listed herein, ranges from any lower limit to any upper limit are contemplated.

The invention claimed is:

1. A process for removing combustible non-volatiles from a reactor system, comprising:
   (A) depositing combustible non-volatiles by pyrolysis at a temperature $\geq 800$° C. of hydrocarbon comprising alkane during a pyrolysis step of duration $t_1$, wherein (a) the combustible non-volatiles are deposited in first and second conduits of a first reactor, (b) the first reactor is located within the reactor system, and (c) the pyrolysis converts at least a portion of the alkane to unsaturated hydrocarbon in the first reactor;
   (B) during a first time interval having a duration $t_{2a}$ of a heating step having a total duration $t_2$,
      (a) conducting a fuel through the first conduit and an oxidant through the second conduit,
      (b) heating the reactor system by combusting at least a portion of the oxidant with (i) at least a portion of the combustible non-volatiles located in the second conduit and (ii) at least a portion of the fuel; and
   (C) during a second time interval having a duration $t_{2b}$ of the heating step, wherein $t_{2a}+t_{2b} \leq t_2$,
      (a) conducting at least a portion of the oxidant through the first conduit,
      (b) reacting the oxidant with at least a portion of the combustible non-volatiles located in the first conduit,
      (c) conducting the fuel through a third conduit of the first reactor,
      (d) conducting a second portion of the oxidant through the second conduit, and
      (e) heating the reactor system by combusting at least a portion of the oxidant with (i) at least a portion of the combustible non-volatiles located in the first and/or second conduits and (ii) at least a portion of the fuel; wherein the first, second, and third conduits comprise at least one channel in a reactor bed.

2. The process of claim 1, wherein $t_1$ is the range of 0.1 seconds to 10.0 seconds.

3. The process of claim 1, wherein $t_2$ is in the range of 0.1 seconds to 10.0 seconds.

4. The process of claim 1, wherein $t_{2a}$ is substantially the same as $t_{2b}$.

5. The process of claim 1, wherein the heating steps (B) and (C) together heat at least part of the reactor system to a temperature $\geq 800$° C. for the pyrolysis.

6. The process of claim 5, wherein step (A) further comprises:
   transferring at least a portion of the unsaturated hydrocarbon away from the reactor via the first and second conduits, wherein at least a portion of the depositing of the combustible non-volatiles occurs during the transfer.

7. The process of claim 6, further comprising repeating steps (A)-(C).

* * * * *